(12) United States Patent
Lawrence et al.

(10) Patent No.: US 8,758,593 B2
(45) Date of Patent: *Jun. 24, 2014

(54) ELECTROCHEMICAL SENSOR

(75) Inventors: Nathan Lawrence, Huntingdon (GB); Valerie Lafitte, Cambridge (GB)

(73) Assignee: Schlumberger Technology Corporation, Sugar Land, TX (US)

(*) Notice: Subject to any disclaimer, the term of this patent is extended or adjusted under 35 U.S.C. 154(b) by 114 days.

This patent is subject to a terminal disclaimer.

(21) Appl. No.: 12/852,315

(22) Filed: Aug. 6, 2010

(65) Prior Publication Data

US 2011/0048969 A1  Mar. 3, 2011

Related U.S. Application Data

(63) Continuation-in-part of application No. 11/781,546, filed on Jul. 23, 2007, now Pat. No. 8,177,958, which is a continuation-in-part of application No. 10/585,263, filed as application No. PCT/GB2004/005397 on Dec. 22, 2004, now Pat. No. 7,901,555.

(30) Foreign Application Priority Data

Jan. 8, 2004 (GB) .................................. 0400325.7

(51) Int. Cl.
  *G01N 27/327* (2006.01)
(52) U.S. Cl.
  USPC ... 205/787.5; 205/792; 205/793; 204/403.03; 204/403.06; 204/412; 204/415; 204/416; 204/433
(58) Field of Classification Search
  USPC .......... 204/403.03, 403.06, 403.13, 406, 407, 204/412, 415, 416, 419, 433; 205/787.5, 205/792, 793
  See application file for complete search history.

(56) References Cited

U.S. PATENT DOCUMENTS

| | | | |
|---|---|---|---|
| 3,780,575 A | 12/1973 | Urbanosky | |
| 3,859,851 A | 1/1975 | Urbanosky | |
| 3,915,831 A | 10/1975 | Riseman et al. | |
| 3,988,233 A | 10/1976 | Gamer et al. | |
| 4,490,234 A | 12/1984 | Buzza | |
| 4,699,892 A | 10/1987 | Suzuki | |
| 4,994,671 A | 2/1991 | Safinya et al. | |
| 5,005,406 A | 4/1991 | Jasinski et al. | |

(Continued)

FOREIGN PATENT DOCUMENTS

| | | |
|---|---|---|
| DE | 275924 A | 2/1990 |
| DE | 10251183 A1 | 7/2003 |

(Continued)

OTHER PUBLICATIONS

Ward et al. ("A new amperometric glucose microsensor: in vitro and short-term in vivo evaluation") Biosensors & Bioelectronics 17 (2002) p. 181-189.*

(Continued)

*Primary Examiner* — Susan D Leong

(57) ABSTRACT

An electrochemical sensor and a method for using an electrochemical sensor are described where the electrochemical sensor comprises a working electrode having thereon one or more redox species that are sensitive to an analyte to be measured and a polymer coating that provides for interaction between the redox species and the analyte.

33 Claims, 14 Drawing Sheets

(56) References Cited

U.S. PATENT DOCUMENTS

| | | | |
|---|---|---|---|
| 5,133,856 A * | 7/1992 | Yamaguchi et al. | 204/416 |
| 5,223,117 A * | 6/1993 | Wrighton et al. | 204/415 |
| 5,286,364 A * | 2/1994 | Yacynych et al. | 205/83 |
| 5,351,532 A | 10/1994 | Hager | |
| 5,445,228 A | 8/1995 | Rathmell et al. | |
| 5,489,371 A | 2/1996 | Joseph et al. | |
| 5,499,528 A | 3/1996 | Bahar | |
| 5,517,024 A | 5/1996 | Mullins et al. | |
| 5,518,390 A | 5/1996 | Nakamura et al. | |
| 5,518,590 A | 5/1996 | Fang | |
| 5,624,546 A | 4/1997 | Milco | |
| 5,667,558 A | 9/1997 | Bryan et al. | |
| 5,676,820 A * | 10/1997 | Wang et al. | 205/777.5 |
| 5,736,650 A | 4/1998 | Hiron et al. | |
| 5,829,520 A | 11/1998 | Johnson | |
| 6,023,340 A | 2/2000 | Wu et al. | |
| 6,262,941 B1 | 7/2001 | Naville | |
| 6,355,166 B1 * | 3/2002 | Amarasinghe et al. | 210/223 |
| 6,374,136 B1 * | 4/2002 | Murdock | 604/20 |
| 6,451,603 B1 | 9/2002 | Atkins et al. | |
| 6,584,827 B2 | 7/2003 | Kiesele et al. | |
| 6,939,717 B2 | 9/2005 | Jiang et al. | |
| 7,407,566 B2 | 8/2008 | Jiang et al. | |
| 7,758,734 B2 | 7/2010 | Jiang et al. | |
| 7,901,555 B2 * | 3/2011 | Jiang et al. | 204/416 |
| 8,177,958 B2 | 5/2012 | Lawrence et al. | |
| 2001/0032785 A1 * | 10/2001 | Cha et al. | 204/435 |
| 2002/0090632 A1 | 7/2002 | Buck et al. | |
| 2003/0089623 A1 * | 5/2003 | Peat et al. | 205/775 |
| 2003/0134426 A1 | 7/2003 | Jiang et al. | |
| 2003/0206026 A1 | 11/2003 | Diakonov et al. | |
| 2004/0118682 A1 * | 6/2004 | Murray et al. | 204/418 |
| 2006/0054501 A1 | 3/2006 | Jiang et al. | |
| 2006/0243603 A1 | 11/2006 | Jiang et al. | |
| 2007/0272552 A1 | 11/2007 | Jiang et al. | |
| 2008/0023328 A1 * | 1/2008 | Jiang et al. | 204/407 |
| 2008/0035481 A1 | 2/2008 | McCormack et al. | |
| 2009/0159464 A1 * | 6/2009 | Hyland et al. | 205/790 |
| 2009/0178921 A1 | 7/2009 | Lawrence et al. | |
| 2010/0243480 A1 | 9/2010 | Jiang et al. | |

FOREIGN PATENT DOCUMENTS

| | | |
|---|---|---|
| EP | 629854 A2 | 12/1994 |
| GB | 2362469 A | 11/2001 |
| GB | 2391314 A | 2/2004 |
| GB | 2397651 A | 7/2004 |
| WO | WO9900575 A2 | 1/1999 |
| WO | WO2004011929 A1 | 2/2004 |
| WO | WO2005066618 A1 | 7/2005 |

OTHER PUBLICATIONS

Combined Search and Exam Report of British Patent Application No. GB0400325.7 dated May 28, 2004: 1-5.

Carter et al., "Voltammetric studies of the interaction of tris (1,10-phenanthroline)-cobalt (III) with DNA," J. Am. Chem. Soc., 1987, vol. 109: pp. 7528-7530.

Casimiri et al., "Co-immobilized L-lactate oxidase and L-lactate dehydrogenase on a film mounted on oxygen electrode for highly sensitive L-lactate determination," Biosensors & Bioelectronics, 1996, vol. 11(8): pp. 783-789.

Downard, "Electrochemically assisted covalent modification of carbon electrodes," Electroanalysis, 2000, vol. 12: pp. 1085-1096.

Galster, "pH measurement: fundamentals, methods, applications, instrumentation," VCH Weinheim: New York, Ed. Ebel, 1991: pp. 20-28.

Hickman et al., "Molecular self-assembly of two-terminal voltammetric microsensors with internal references," Science, 1991, vol. 252: pp. 688-691.

Kuo et al., "Electrochemical Modification of Boron-Doped Chemical Vapor DepositedDiamond Surfaces with Covalently Bonded Monolayers," Electrochemical and Solid-State Letters, 1999, vol. 2(6): pp. 288-290.

Lawrence et al., "Amperometric detection of sulfide at a boron doped diamond electrode: the electrocatalytic reaction of sulfide with ferricyanide in aqueous solution," Electroanalysis, 2002, vol. 14(7-8): pp. 499-504.

Lawrence et al., "The electrochemical analog of the methylene blue reaction: a novel amperometric approach to the detection of hydrogen sulfide," Electroanalysis, 2000, vol. 12(18): pp. 453-1 460.

Lawrence et al., "Voltammetric characterization of a N,N'-Diphenyl-p-phenylenediamine-loaded screen-printed electrode: a disposable sensor for hydrogen sulfide," Anal. Chem., 2003, vol. 75: pp. 2054-2059.

Pandurangappa et al., "Physical adsorption of N,Na-diphenyl-p-phenylenediamine onto carbon particles: Application to the detection of sulfide," The Analyst, 2003, vol. 128: pp. 473-479.

Rhodes, "Determination of hydrogen sulfide content in natural gas, evaluation of containers for preparation of calibration standards, and sample collection procedure," Report of Investigations No. 8391, U.S. Department of the Interior, Bureau of Mines, 1979: pp. 1-12.

Anonymous, "Wireline Formation Testing and Sampling," Schlumberger, 1996: pp. 10-1 to 10-25.

Scholz et al., "Voltammetry of solid microparticles immobilized on electrode surfaces," Journal of Solid State Electrochemistry, 1998, vol. 20: pp. 1-87.

Solodov et al., "Distribution and geochemistry of contaminated subsurface waters in fissured volcanogenic bed rocks of the Lake Karachai area, Chelyabinsk, Southern Urals," Lawrence Berkeley Laboratory Report, Jun. 1994, LBL# 36780/UC-603: pp. 1-46.

Wadhawan et al., "Voltammetric characteristics of graphite electrodes modified with microdroplets of n-butylferrocene," Journal of Electroanalytical Chemistry, 2002, vol. 533 pp. 71-84.

Wang et al., "Carbon nanotube screen-printed electrical sensors," Analyst, 2004, vol. 129: pp. 1-2.

Wildgoose et al., "Anthraquinone-derivatised carbon powder: reagentless voltammetric pH electrodes," Talanta, 2003, vol. 60: pp. 887-893.

PCT Search Report for PCT/GB2004/005397; Mar. 23, 2005.

PCT Preliminary Examination Report for PCT/GB2004/005397; issued Jul. 10, 2006.

* cited by examiner

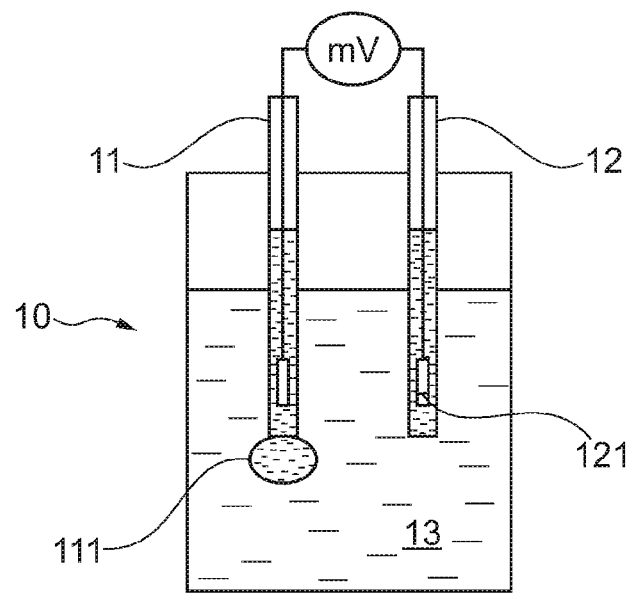
Fig. 1
(Prior Art)
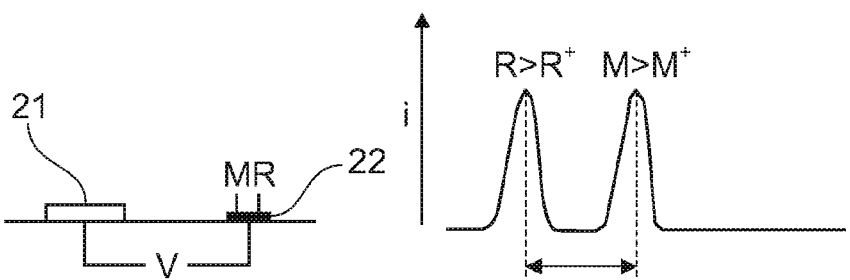
Fig. 2A
(Prior Art)
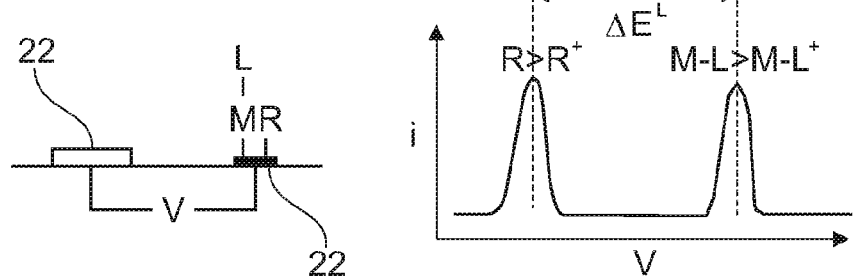
Fig. 2B
(Prior Art)
Fig. 2C
(Prior Art)

Scheme 1

Scheme 2

ELECTROCHEMICAL SENSOR

This application claims the benefit of and is a continuation in part of U.S. application Ser. No. 11/781,546 (Publication No. 2008/0023328) filed on Jul. 23, 2007 (which itself is a continuation-in-part of U.S. application Ser. No. 10/585,263 filed on May 17, 2007 as 371 of International Application No. PCT/GB04/05397), and each of these referenced applications are hereby incorporated by reference in their entirety for all purposes.

BACKGROUND

Embodiments of the present invention relate to an electrochemical sensor for detecting and monitoring analytes. More specifically, but not by way of limitation, certain embodiments of the present invention provide methods of operating an electrochemical sensor to and an electrochemical sensor for, among other things, determining pH and analyzing ion content of fluids. In other embodiments, the electrochemical sensor and methods may be used to detect and measure analytes such as hydrogen sulphide, oxygen, carbon dioxide, nitrates and/or the like.

The detection and/or measurement of analyte concentration, for example particular hydrogen ion concentration or pH, are important, in a number of research, industrial, and manufacturing processes. Merely way of example, pH measurement is important in the pharmaceutical industry, the food and beverage industry, the treatment and management of water and waste, chemical and biological research, hydrocarbon production, water monitoring and/or the like. Moreover, there has been a long felt need across numerous industries for better analyte sensing techniques, especially pH detection.

In the hydrocarbon industry, analysis operations may obtain an analysis of downhole fluids usually through wireline logging using a formation tester such as the MDT™ tool of Schlumberger Oilfield Services. However, more recently, it was suggested to analyze downhole fluids either through sensors permanently or quasi-permanently installed in a wellbore or through sensors mounted on the drillstring. The latter method, if successfully implemented, has the advantage of obtaining data while drilling, whereas the former installation could be part of a control system for wellbores and hydrocarbon production therefrom.

To obtain an estimate of the composition of downhole fluids, the MDT tools may use an optical probe to estimate the amount of hydrocarbons in the samples collected from the formation. Other sensors use resistivity measurements to discern various components of the formations fluids.

Particularly, knowledge of downhole formation (produced) water chemistry is needed to save costs and increase production at all stages of oil and gas exploration and production. Knowledge of particularly the water chemistry is important for a number of key processes of the hydrocarbon production, including:

- Prediction and assessment of mineral scale and corrosion;
- Strategy for oil/water separation and water re-injection;
- Understanding of reservoir compartmentalization/flow units;
- Characterization of water break-through;
- Derivation of the water cut $R_w$; and
- Evaluation of downhole the $H_2S$ partition the oil and or water (if used for $H_2S$ measurements).

Some chemical species dissolved in water (including, for example, $Cl^-$ and $Na^+$) do not change their concentration when removed to the surface either as a part of a flow through a well, or as a sample taken downhole. Consequently information about their quantities may be obtained from downhole samples and in some cases surface samples of a flow. However, the state of chemical species, such as $H^+$ (pH=−log [concentration of $H^+$]), $CO_2$, or $H_2S$ may change significantly while tripping to the surface. The change occurs mainly due to a difference in temperature and pressure between downhole and surface environment. In case of sampling, this change may also happen due to degassing of a sample (seal failure), mineral precipitation in a sampling bottle, and (especially in case of $H_2S$)—a chemical reaction with the sampling chamber. It should be stressed that pH, $H_2S$, or $CO_2$ are among the most critical parameters for corrosion and scale assessment. Consequently it is of considerable importance to know their downhole values precisely.

The concentration of protons or its logarithm pH can be regarded as the most critical parameter in water chemistry. It determines the rate of many important chemical reactions as well as the solubility of chemical compounds in water, and (by extension) in hydrocarbon.

Analyzing samples representative of downhole fluids is an important aspect of determining the quality and economic value of a hydrocarbon formation. Similarly, analyzing properties of liquids associated with an aquifer may be important in aquifer analysis in the hydrocarbon, water production industries and/or resource management.

Electrochemical sensors using redox active species, while having advantages over potentiometric sensors, may themselves have operability issues. For example, in the food and beverage industry, the water monitoring/management industry, the biotech industry and/or the like, it may not be desirable or even allowable in accordance with regulations to have the redox active species leech/diffuse from the electrochemical sensor. Moreover, handing of sensors comprising certain redox species may be an issue. Further, leeching/removal of the redox species from the sensor may affect performance of the sensor. In addition, it may be difficult/costly to fabricate an electrochemical sensor comprising redox species. Another issue is that electrochemical sensors using microelectrode designs may be easily fouled etc. and/or may have fabrication and/or operation issues.

The present invention provides an apparatus and method for performing electrochemical measurements. More specifically, the present invention provides a robust electrochemical sensor for accurate ion selective electrochemical measurements, including pH measurements.

SUMMARY

Embodiments of the present invention provide an electrochemical sensor comprising one or more redox species sensitive to an analyte coupled with a working electrode to provide for detection/measurement of the analyte.

In one embodiment of the present invention, the sensor may comprise a redox species. Merely by way of example, the redox species may be based on anthraquinone redox chemistry.

In certain embodiments of the present invention, a working electrode for an electrochemical sensor is provided, the working electrode comprising:
- a conducting substrate;
- a first set of redox species coupled with the conducting substrate, wherein the first set of redox species comprises one or more redox species that are sensitive to an analyte; and
- a polymer layer covering at least an area of the conducting substrate coupled with the first set of redox species and configured to allow for an interaction between the first set of redox species and the analyte and to prevent diffusion of the first set of redox species from the working electrode.

In certain aspects, the working electrode may further comprise a second set of redox species disposed between the substrate and the polymer layer, wherein the polymer layer is configured to prevent diffusion of the second set of redox species from the working electrode.

In some embodiments, the first set of redox species is chemically bound to the conducting substrate of the working electrode.

In one aspect of the present invention, the polymer layer coating the working electrode may comprise a polystyrene polymer. In another aspect of the present invention, the polymer layer coating the working electrode may comprise a polysulphone polymer. By way of example, in some embodiments, the working electrode may have a diameter between 1 and 5 millimeters and the polymer layer may comprise less than 600 micrograms of the polystyrene polymer. In other embodiments, the working electrode may have a diameter between 1 and 5 millimeters and the polymer layer may comprise less than 600 micrograms of the polysulphone polymer.

In accordance with one embodiment of the present invention, an electrochemical sensor for detecting or measuring an analyte in a fluid is provided, the electrochemical sensor comprising:
a working electrode, the working electrode comprising a first set of redox species, a second set of redox species and a polymer layer, wherein:
the first set of redox species comprises one or more redox species that are sensitive to the analyte;
the second set of redox species comprises one or more redox species that are insensitive to the analyte; and
the polymer layer is configured to prevent diffusion of at least one of the first and the second sets of redox species from the working electrode and to allow for an interaction between at least the first set of redox species and the analyte;
a counter electrode;
a reference electrode;
means to apply a varying potential to the working electrode;
means to measure a potential difference between the working electrode and the reference electrode;
means to measure a current flow between the working electrode and the counter electrode as the applied potential causes the first and the second set of redox species to undergo at least one of oxidation and reduction; and
a processor configured to process a presence or a measurement of the analyte from at least one of the measured potential difference and the measured current.

In aspects of the present invention, the processor of the electrochemical sensor may processes the presence or measurement of the analyte from peak current flows produced by the oxidation or reduction of the first and the second sets of the redox species.

In one embodiment of the present invention, the electrochemical sensor may comprise a first working electrode and a second working electrode where the first working electrode comprises the first set of redox species and the second working electrode comprises the second set of redox species.

In an embodiment of the present invention, the electrochemical sensor may comprise a working electrode having a diameter between 1 and 5 millimeters and coated with a polymer layer comprises less than 1000 micrograms of polymer.

In certain aspect, the electrodes of the electrochemical sensor may have diameters of the order of millimeters. In such aspects, the polymer coating may comprise less than 1000 micrograms of polymer, such an amount of polymer providing for prevention of leeching, diffusion or the like of the redox species into the fluid and, at the same time providing for interaction between the analyte and the redox species. In other aspects, smaller quantities of polymer may be used, for example less than 600 micrograms of polymer may be used for a stable working electrode where rapid response time is not an issue and between 10 and 400 micrograms of polymer may be used where a quick response time is required. The polymer may comprise polystyrene, polysulphone and/or the like.

In some embodiments of the present invention, the electrochemical sensor may comprise a working electrode having a diameter between 1 and 5 millimeters and coated with a polymer layer comprising less than 600 micrograms of a polystyrene polymer. In other embodiments of the present invention, the electrochemical sensor may comprise a working electrode having a diameter between 1 and 5 millimeters and coated with a polymer layer comprising less than 600 micrograms of the polysulphone polymer.

In an embodiment of the present invention, a separate/independent reference electrode is used. In certain aspects, a potential difference between the working electrode and the reference electrode may be measured and used to get a scale for the voltammetric measurements and/or negate any shift in the response of the redox species. Furthermore, use of the separate/independent reference electrode may provide that a first surface area of the counter electrode may be of the order of one to ten times or one to a hundred times that of a second surface area of the working electrode. In certain, aspects the macro size of the working electrode may, among other things, increase the effectiveness, ease of manufacture and/or accuracy of the electrochemical sensor.

In certain aspects, the electrochemical sensor includes a temperature probe for measuring a temperature of the fluid. The temperature measurement may be used to calibrate the electrochemical sensor.

In one embodiment of the present invention, a method for electrochemically measuring an analyte in a fluid is provided, the method comprising:
contacting a working electrode with the fluid, wherein the working electrode comprises a conducting substrate coupled with a first set of redox species that are sensitive to the analyte and a second set of redox species that are insensitive to the analyte and a polymer layer;
using the polymer layer to prevent diffusion of at least one of the first set of redox species and the second set of redox species from the working electrode;
applying a varying potential between the working electrode and the reference electrode;
making voltammetric measurements of at least a current flow between the working electrode and the counter electrode as the varying potential causes the first and the second set of redox species to undergo at least one of oxidation and reduction and a potential difference between the working electrode and the reference electrode; and
processing the measurement of the analyte from the voltammetric measurements.

In another embodiment of the present invention, a method of manufacturing a working electrode for an electrochemical sensor for detecting or measuring an analyte in a fluid is provided, the method comprising:

coupling at least a portion of the working electrode with a first set of redox species sensitive to the analyte;

depositing a second set of redox species insensitive to the analyte on the working electrode; and coating at least a portion of the working electrode with a polymer.

In some aspects, the method of manufacture may use solvent casting of the second redox species on the working electrode followed by deposition of the polymer layer over the working electrode. The polymer layer may provide for holding the redox species in contact with the conducting substrate and/or preventing loss of the redox species from the working electrode allowing for many different types of manufacturing process to be used to position the redox species at and/or couple the redox species with the working electrode.

In some embodiments of the present invention, the substrate onto which the redox species is mounted may be based on carbon in one of its elementary forms such as graphite, carbon powder, diamond. In a variant, the substrate may be derivatised nanotubes, including multi-walled nanotubes or the like. In other embodiments, other substrates may be used for the electrochemical sensor.

An electrochemical technique using a method or sensor in accordance with the present invention may be applied for example as part of a production logging tool, an open hole formation tester tool (such as the Modular Dynamic Tester, MDT™), an aquifer analyzing tool and/or the like. In certain aspects, the technique according to certain embodiments of the present invention may provide a downhole real-time water sample validation or downhole pH measurement which may be used for predicting mineral scale, corrosion assessment and/or the like.

These and other features of the invention, embodiments and variants thereof, possible applications and advantages may become appreciated and understood by those skilled in the art from the following detailed description and drawings.

BRIEF DESCRIPTION OF DRAWINGS

The present disclosure is described in conjunction with the appended figures:

FIG. 1 shows a schematic diagram of the main elements of a known voltametric sensor;

FIGS. 2A-C show schematic-type diagrams of the main elements of a known electrochemical microsensor and its operation;

DETAILED DESCRIPTION

Figure 3:
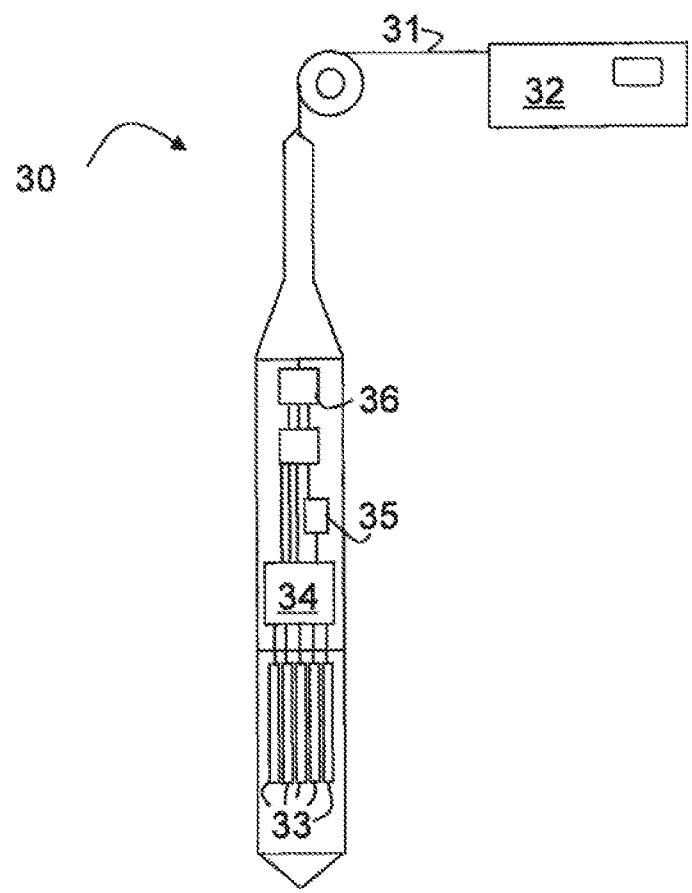
FIG. 3 shows a schematic diagram of a known downhole probe using potentiometric sensors.

The ensuing description provides exemplary embodiments of the present invention only, and is not intended to limit the scope, applicability or configuration of the invention. Rather, the ensuing description of the exemplary embodiments will provide those skilled in the art with an enabling description for implementing an embodiment of the invention. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments maybe practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

In the following description, the term sensitive means that the redox system reacts with an analyte to undergo reduction/oxidation and/or the redox system undergoing reduction/oxidation is perturbed by the presence and concentration of the analyte under an applied potential difference.

An electrochemical sensor comprising redox active species provides an effective way of measuring analytes. By applying a polymer to a sensing/working electrode(s) of the electrochemical sensor a synergistic effect is produced wherein the redox species and the analyte can still interact, notwithstanding the presence of the polymer layer, and the polymer layer acts to maintain the redox species at the working/sensing electrode. By using a polymer layer to maintain the redox species at the working/sensing electrode different efficient and effective methods for manufacturing the electrochemical sensor may be used.

The theory of voltammetry and its application to surface water measurements at ambient temperatures are both well developed. The method is based on the measurement of the electromotive force (e.m.f.) or potential E in a potentiometric cell which includes measuring and reference electrodes (half-cells).

FIG. 1 shows the general components of a known voltammetric cell 10. A measuring electrode 11 is inserted into a solution 13. This electrode consists of an internal half element (for example, Ag wire covered by an AgCl salt) in a solution of a fixed pH (for example, 0.1 M HCl in some pH electrodes), and an ion-selective membrane 111 (like glass $H^+$ selective membrane in pH glass electrode). The reference electrode 12 also contains an internal half-element (typically the same AgCl;Ag) inserted in a concentrated KCl (for example 3M) solution/gel saturated with $Ag^+$, which diffuses (or flows) through the reference (liquid) junction 121.

The ion-selective electrode 11 measures the potential that arises because of the difference in activity or concentration of a corresponding ion ($H^+$ in case of pH) in the internal solution and in the measured solution. This potential is measured against the reference potential on the reference electrode 12, which is fixed because of a constant composition of a reference solution/gel. The electrodes may be separated (separate half cells), or combined into one ("combination electrode").

The measured e.m.f. is an overall function of the temperature and the activity of an ith ion, to which the measuring electrode is selective:

$$E = E° + (k*T)*\log(a_i),  \quad [1]$$

where E is the measured electromotive force (e.m.f.) of the cell (all potentials are in V), $a_i$ corresponds to the activity of the ith ion and is proportional to its concentration. E° is the standard potential (at temperature T) corresponding to the E value in a solution with the activity of ith ion equal to one. The term in parenthesis is the so-called Nernstian slope in a plot of E as a function of $\log(a_i)$. This slope (or the constant "k") together with the cell (electrode) constant (E°) is experimentally determined via a calibration procedure using standard solutions with known activities of ith ion. For good quality undamaged electrodes this slope should be very close to the theoretical one, equal to (R*T/F*z), where F is the Faraday constant (96485 kJ/mole), R is the gas constant (8.313 j/mole K), $z_i$ is the charge of ith ion.

The Nernst equation [1] can be rewritten for pH sensors, i.e. log a($H^+$) as $$E_{0.5} = K - (2.303\ RTm/nF)pH \quad [2]$$

where $E_{0.5}$ is the half-wave potential of the redox species involved, K is an arbitrary constant, R is the ideal gas constant, m is the number of protons and n is the number of electrons transferred in the redox reaction.

In FIG. 3, there are schematically illustrated elements of a known downhole analyzing tool 30. The body of the tool 30 is connected to the surface via a cable 31 that transmits power and signals. A computer console 32 controls the tool, monitors its activity and records measurements. The tool 30 includes a sensor head with at number of selective electrochemical probes 33 each sensitive to a different molecular species. Also housed in the body of the tool are further actuation parts 34 that operate the head, a test system 35 and transceivers 36 to convert measurements into a data stream and to communicate such data stream to the surface. The electrodes are located at the bottom part of the probe and include those for pH, Eh (or ORP), $Ca^{2+}$ (pCa), $Na^+$ (pNa), $S^{2-}$ (pS), $NH_4^+$ (p$NH_4$), and reference electrode (RE). $H_2S$ partial pressure may be calculated from pH and pS readings.

In the following aspects and elements of certain embodiments of the present invention are described in detail.

In an embodiment of the present invention, an anthraquinone may be homogenously derivatised onto carbon particles (AQC)

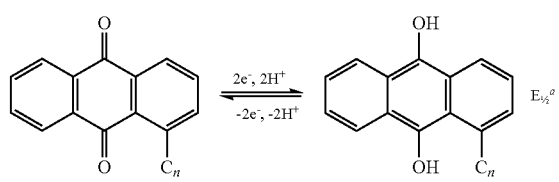

The AQC system is derived using 2 g of carbon powder (1.5 μm in mean diameter) mixed with a 10 cm³ solution containing 5 mM Fast Red AL Salt (Anthraquinone-1-diazonium chloride) to which 50 mM hypophosphorous acid (50%) is added. The reaction is allowed to stand with occasional stirring at 5° C. for 30 minutes, after which it is filtered by water suction. Excess acid is removed by washing with distilled water and with the powder being finally washed with acetonitrile to remove any unreacted diazonium salt in the mixture. It is then air dried by placing inside a fume hood for a period of 12 hours and finally stored in an airtight container.

In a similar manner, phenanthrenequinone (PAQ)

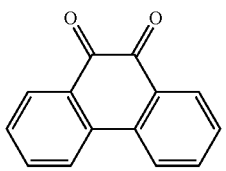

may be prepared as a molecular species to be attached to an electrode to undergo a redox reaction.

Alternatively, N,N'-diphenyl-p-phenylenediamine (DPPD) spiked onto carbon particles undergoes a redox process as shown below:

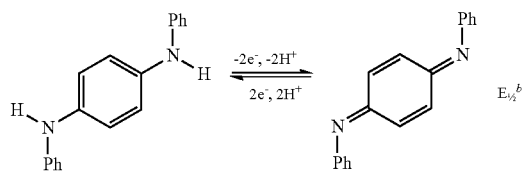 [SMILES: c1ccc(Nc2ccc(Nc3ccccc3)cc2)cc1 ; C1=CC(=Nc2ccccc2)C=CC1=Nc1ccccc1]

The bonding of DPPD onto carbon is achieved by mixing 4 g of carbon powder with 25 mL of 0.1M HCl+0.1M KCl and 20 mM DPPD solution in acetone. The reaction mixture is stirred continuously for 2 hours in a beaker and then filtered after which it was washed with distilled water to remove excess acid and chloride. It is then air dried by placing inside a fume hood for 12 hours and finally stored in an airtight container.

In a static environment, where the sensor surface is not exposed to a flow, it is possible to immobilize water insoluble DPPD crystals directly onto the electrode surface. However in the non-static environment it is preferred to link the sensitive molecules via a chemical bond to such a surface.

In some embodiments, the derivatised carbon powders may be immobilized onto a basal plane pyrolytic graphite (BPPG) electrode prior to voltammetric characterization following a procedure described by Scholz, F. and Meyer, B., "Voltammetry of Solid Microparticles Immobilised on Electrode Surfaces in Electroanalytical Chemistry" ed. A. J. Bard, and I. Rubenstein, Marcel Dekker, New York, 1998, 20, 1. Initially the electrode is polished with glass polishing paper (H00/240) and then with silicon carbide paper (P1000C) for smoothness. The derivatised carbons are first mixed and then immobilized onto the BPPG by gently rubbing the electrode surface on a fine qualitative filter paper containing the functionalized carbon particles.

Figure 4A:
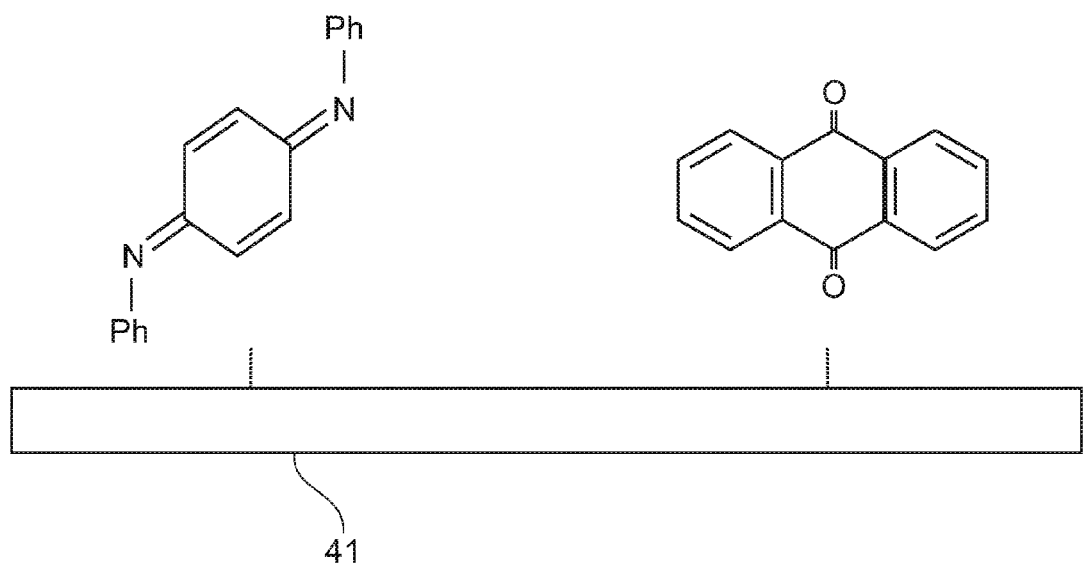
FIG. 4A illustrates the surface structure of a measuring electrode in accordance with an embodiment of the present invention.

The resulting modified electrode surface is schematically illustrated by FIG. 4A showing an electrode 41 with bonded DPPD and AQC.

In some embodiments, an internal pH reference involving a pH independent redox couple may be used to increase the stability of any voltammetric reading, hence circumventing uncertainties caused by drift of the external reference electrode. In such a configuration, the sensor may in some aspects include two reference electrodes.

A suitable reference molecule may be, for example, $K_5Mo(CN)_8$ or various ferrocene containing molecules, which both have a stable redox potential ($K_5Mo(CN)_8$ at around 521 mV) that is sufficiently separated from expected shifting of redox signals of the two indicator species over the pH range of interest. As shown in Table 1 that both the oxidation and reduction potentials of $K_5Mo(CN)_8$ are fairly constant across the entire pH range

TABLE 1

| pH | $AQ_{OX}$ | $AQ_{RED}$ | $DPPD_{OX}$ | $DPPD_{RED}$ | $Mo\text{-}_{OX}$ | $Mo\text{-}_{RED}$ |
| --- | --- | --- | --- | --- | --- | --- |
| 4.6 | −0.440 | −0.448 | 0.202 | 0.224 | 0.524 | 0.524 |
| 6.8 | −0.576 | −0.580 | 0.094 | 0.082 | 0.528 | 0.522 |
| 9.2 | −0.710 | −0.674 | −0.204 | −0.372 | 0.512 | 0.508 |

The Mo-based reference species can be retained in the solid substrate via ionic interactions with co-existing cationic polymer, such as poly (vinyl pyridine), that was spiked into the solid phase. Other pH independent species, such as ferrocyanide may also be used, however, the redox peaks may be obscured by the signals of the measuring redox species.

Figure 4B:
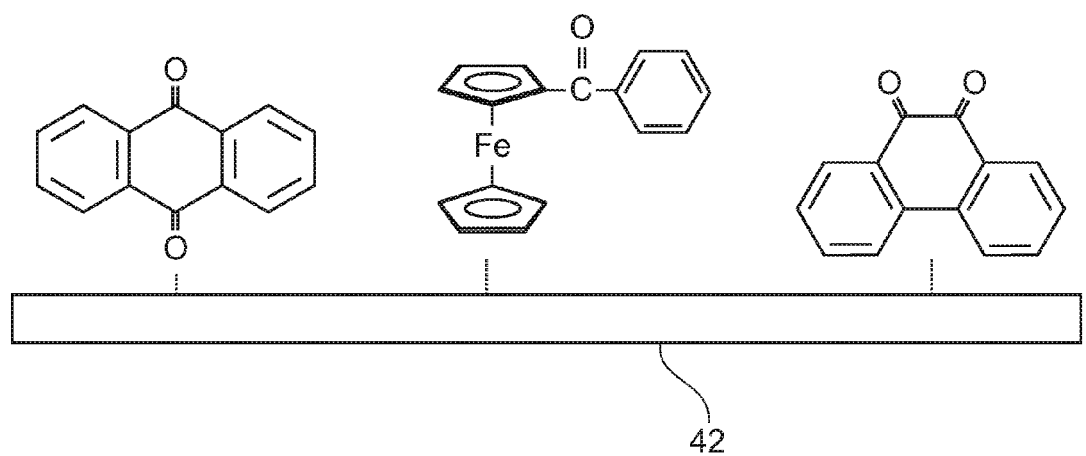
FIG. 4B illustrates the surface structure of a measuring electrode with an internal reference electrode in accordance with an embodiment of the present invention.

In FIG. 4B the electrode 42 carries bonded molecules AQC and PAQ together with PVF as an internal reference molecule.

The most common forms of conducting carbon used in electrode manufacture are glassy carbon, carbon fibres, carbon black, various forms of graphite, carbon paste and carbon epoxy. One further form of carbon, which has seen a large expansion in its use in the field of electrochemistry since its discovery in 1991 is the carbon nanotube (CNT). The structure of CNTs approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other.

Figure 4C:
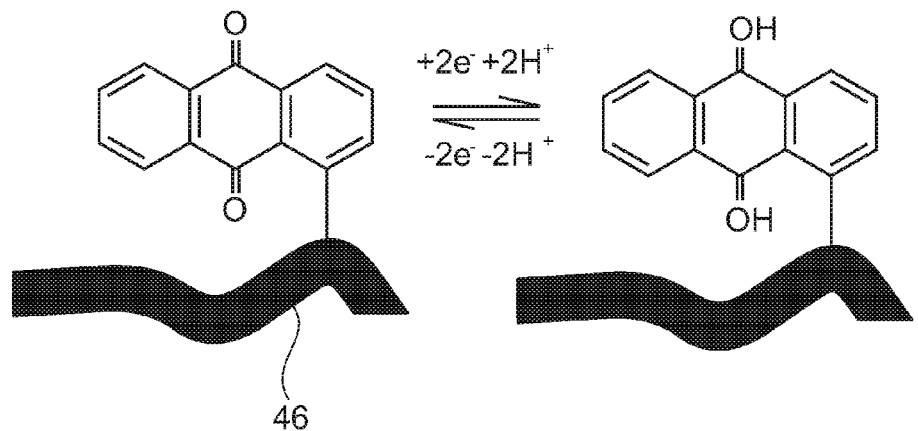
FIG. 4C illustrates the redox reaction of a measuring electrode in accordance with another embodiment of the present invention using multi-walled carbon nanotubes.
Figure 4D:
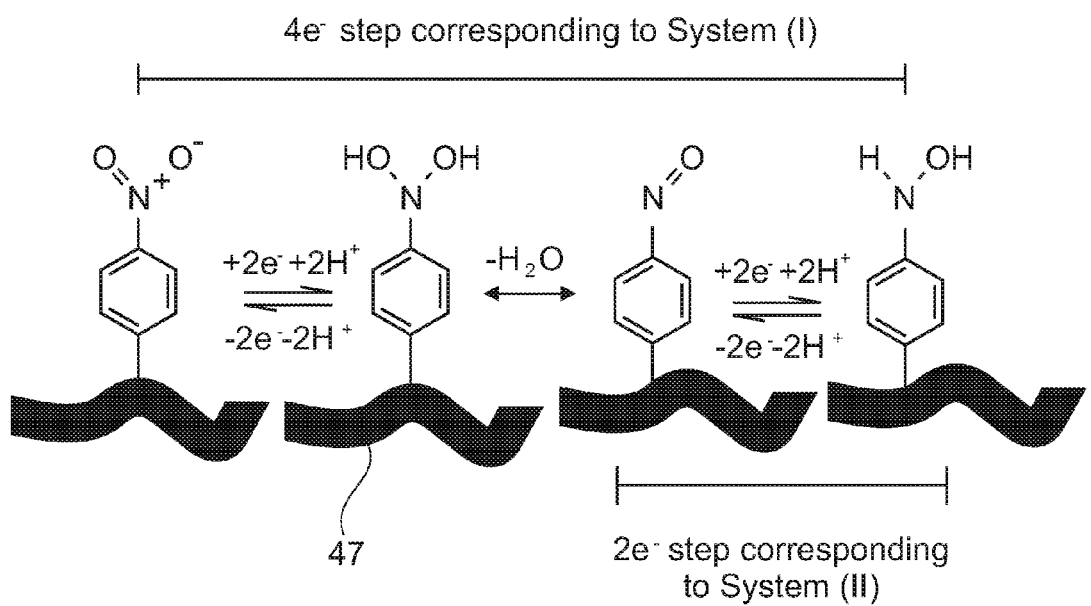
FIG. 4D illustrates the redox reaction of a measuring electrode with internal reference electrode in accordance with another embodiment of the present invention; using multi-walled carbon nanotube.

The above activation methods for binding a redox active species to graphite or carbon surfaces can be extended via the chemical reduction of aryldiazonium salts with hypophosphorous acid, to include the covalent derivatization of MWCNTs by anthraquinone-1-diazonium chloride and 4-nitrobenzenediazonium tetrafluoroborate. This results in the synthesis of 1-anthraquinonyl-MWCNTs (AQ-MWCNTs) and 4-nitrophenyl-MWCNTs (NB-MWCNTs) as shown in FIGS. 4C and 4D, respectively. The respective substrates 46 and 47 are multi-walled carbon nanotubes.

The preparation process of the derivatised MWCNT involves the following steps: first 50 mg of MWCNTs are stirred into 10 cm³ of a 5 mM solution of either Fast Red AL (anthraquinone-1-diazonium chloride) or Fast Red GG (4-nitrobenzenediazonium tetrafluoroborate), to which 50 cm³ of hypophosphorous acid ($H_3PO_2$, 50% w/w in water) is added. Next the solution is allowed to stand at 5° C. for 30 minutes with gentle stirring. After which, the solution is filtered by water suction in order to remove any unreacted species from the MWCNT surface. Further washing with deionized water is carried out to remove any excess acid and finally with acetonitrile to remove any unreacted diazonium salt from the mixture. The derivatised MWCNTs arethen air-dried by placing them inside a fume hood for a period of 12 hours after which they are stored in an airtight container prior to use. Untreated multi-walled nanotubes can be purchased from commercial vendors, for example from Nano-Lab Inc of Brighton, Mass., USA in 95% purity with a diameter of 30+/−15 nm and a length of 5-20 μm.

The reduction of diazonium salts using hypophosphorous acid as demonstrated is a versatile technique for the derivatization of bulk graphite powder and MWCNTs. This has the advantage over previous methods involving the direct electrochemical reduction of aryldiazonium salts onto the electrode surface, as the chemically activated method allows the possibility for inexpensive mass production of chemically derivatised nanotubes for a variety of applications. Furthermore the derivatization of MWCNTs proffers the possibility of sensor miniaturization down to the nano-scale.

Another way of immobilizing the redox active compounds onto the working electrode terminal may be by packing a mixture of the compounds and carbon powder effectively into a recessed working electrode cavity without a binding substance. The carbon powder could be mixed with the pH-sensitive and reference chemicals and ground finely with a mortar and pestle. Then the empty recess might be filled with the powder mix which would be mechanically compacted. The resulting void in the working electrode recess would then be refilled and compacted again. This would be repeated several times until the recess is full. The material would be pressed such that the particles are packed into a dense matrix.

Although packing of the redox active compounds into a single electrode area (as discussed above) provides a means of forming the sensor it can be envisaged that immobilization of two or more species into various distinct electrodes may provide improved signals and more facile manufacturing. This can be especially thought of when the compounds are chemically attached to the electrode surface via a covalent linkage. In this case a single monolayer of compounds will be formed on the surface.

It can be envisaged that in embodiments of the present invention in which a pH sensitive and a pH insensitive compound are coupled with the working electrode, the compounds may be bulky or undergo differing immobilization rates then formation of the monolayer will favor one or other of the compounds such that the signal is dominated by a single compound and hence the sensor is inoperable. In these cases immobilization of each compound onto separate electrodes would overcome the problem, as the immobilization procedure for each would not be under competitive control. It can therefore be proposed that a sensor in which two or more working electrodes, with different electroactive species immobilized on each surface, is utilized and cross connected such that only a single voltammetric sweep is required.

For embodiments of the present invention, using either a combination of an insensitive redox species and a sensitive redox species or two or more different sensitive redox species, the methods for coupling the redox species to the working electrode discussed above may be used. Additionally, for either of these embodiments, the redox species whether it be sensitive or insensitive may be combined with a binding material or the like, such as an ink or the like, and screen printed onto the working electrode.

Figure 4E:
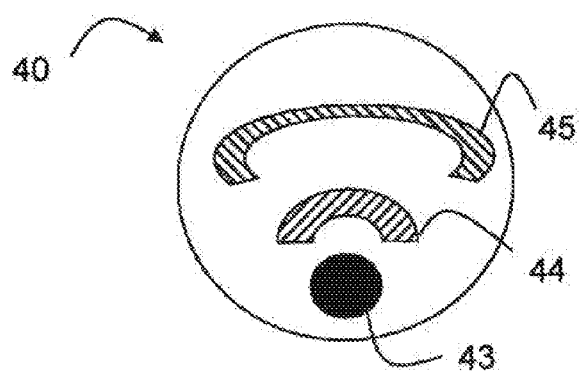
FIG. 4E illustrates the geometrical surface layout of the electrode of FIG. 4B, in accordance with an embodiment of the present invention.

In FIG. 4E there is shown a possible geometric configuration or layout for the sensor surface 40 which is exposed to the fluid to be tested, which may, merely by way of example be a wellbore fluid or the like. The surface includes a working electrode 43 as described in FIG. 4A or 4B, together with the reference electrode 44 and a counter electrode 45. The reference electrode 44, in some aspects of the present invention, may comprise an external electrode.

Figure 5:
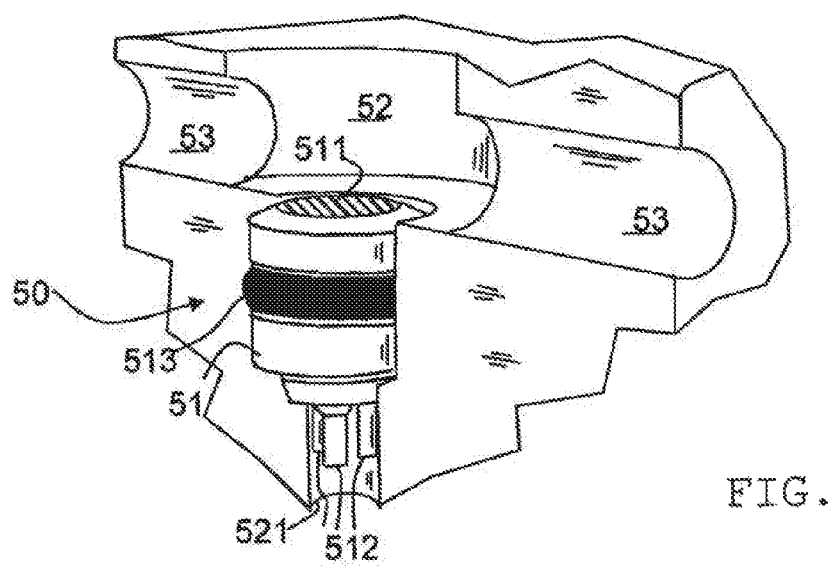
FIG. 5 is a perspective view, partially cut-away, of an electrochemical sensor in accordance with an embodiment of the present invention.

A schematic of a microsensor 05 incorporating a modified surface prepared in accordance with the procedure described above is shown in FIG. 5. The body 51 of the sensor is fixed into the end section of an opening 52. The body carries the electrode surface 511 and contacts 512 that provide connection points to voltage supply and measurement through a small channel 521 at the bottom of the opening 52. A sealing ring 513 protects the contact points and electronics from the fluid to be tested that passes under operation conditions through the sample channel 53.

In some embodiments of the present invention, the electrochemical sensor may include two measuring or indicator electrodes or molecules measuring two e.m.f or potentials with reference to the same reference electrode and being sensitive to the same species or molecule in the environment. As a result, the sensitivity towards a shift in the concentration of the species may increase. Using the above example of AQC and DPPD and the pH (or $H^+$ concentration, the Nernst equation applicable to the new sensor is the sum of the equations describing the individual measuring electrodes. Thus, combining the half wave potential $E_{0.5}(AQC)$ for anthraquinone $$E_{0.5}(AQC)=K(AQC)-(2.303\ RTm/nF)pH \quad [3]$$

with the half wave potential $E_{0.5}(DPPD)$ for N,N'-diphenyl-p-phenylenediamine $$E_{0.5}(DPPD)=K(DPPD)-(2.303\ RTm/nF)pH \quad [4]$$

yields the half wave potential $E_{0.5}(S)$ for the combined system:

$$E_{0.5}(S)=E_{0.5}(AQC)+E_{0.5}(DPPD)=(K(AQC)+K(DPPD))-2*(2.303\ RTm/nF)pH=K(S)-2*(2.303\ RTm/nF)pH \quad [5]$$

Where K(S) is the sum of the two constants K(AQC) and K(DPPD). As the shift of the potential with a change in pH depends on the second term, the (theoretical) sensitivity of the sensor has doubled.

The use of a further (third) redox species sensitive to the same species would in principle increase the sensitivity further. As the method detects shifts in the peak location of the voltammogram, however, more efforts are anticipated to be required to resolve overlapping peaks in such a three-molecule system.

However, in other embodiments of the present invention, a single redox species sensitive to a species may be used in combination with a redox species that is insensitive to the that species This configuration may provide in some circumstances for improved detection of the analyte then by using multiple redox species sensitive to the same species as there are less issues in such a sensor regarding redox peak detection, i.e., the use of multiple species sensitive to the same species requires the detection of multiple peaks on a voltammogram compared with identifying a single peak in a single redox species electrochemical sensor. However, in other circumstances it may be desirable to use an embodiment of the present invention comprising multiple redox species sensitive to the analyte to be detected.

Figure 6:
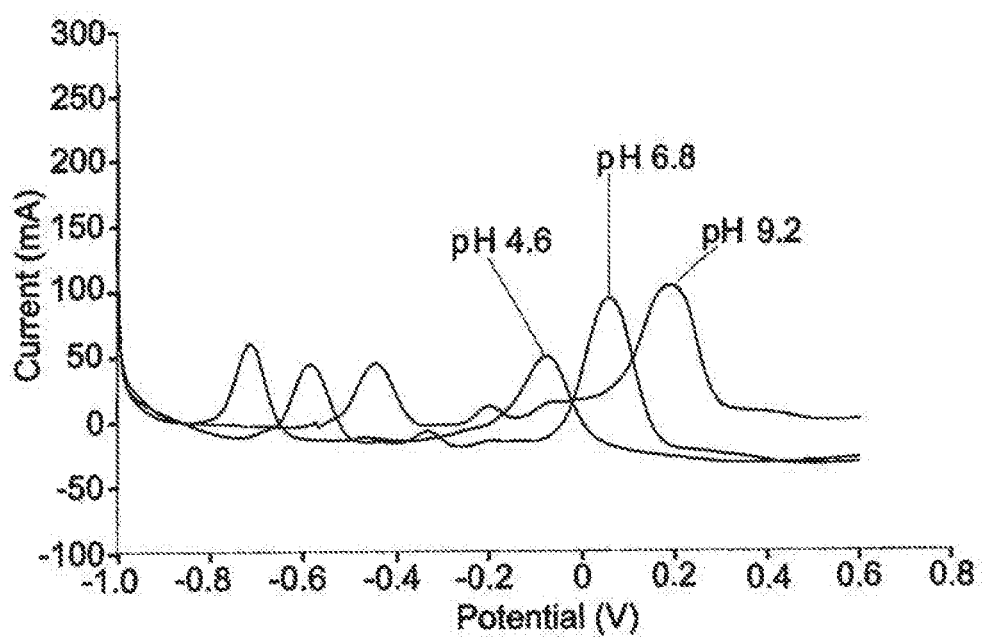
FIG. 6 shows voltammograms recorded from an electrochemical sensor at three different pH values, in accordance with an embodiment of the present invention.

FIG. 6 shows results in a range of pH solutions (pH 4.6, 0.1M acetic acid+0.1M sodium acetate buffer; pH 6.8, 0.025M disodium hydrogen phosphate+0.025M potassium dihydrogen phosphate buffer; pH 9.2, 0.05M disodium tetraborate buffer). The figure presents the corresponding square wave voltammograms when the starting potential was sufficiently negative to have both DPPD and AQ in their reduced forms.

In an embodiment of the present invention, square wave voltammetry may be used to provide for enhanced peak detection. While in certain aspects, linear sweep voltammetry and or cyclic voltammetry may be used for the electrochemical sensor, the use of square wave voltammetry may provide for producing more pronounced redox associated peaks.

Figure 7A:
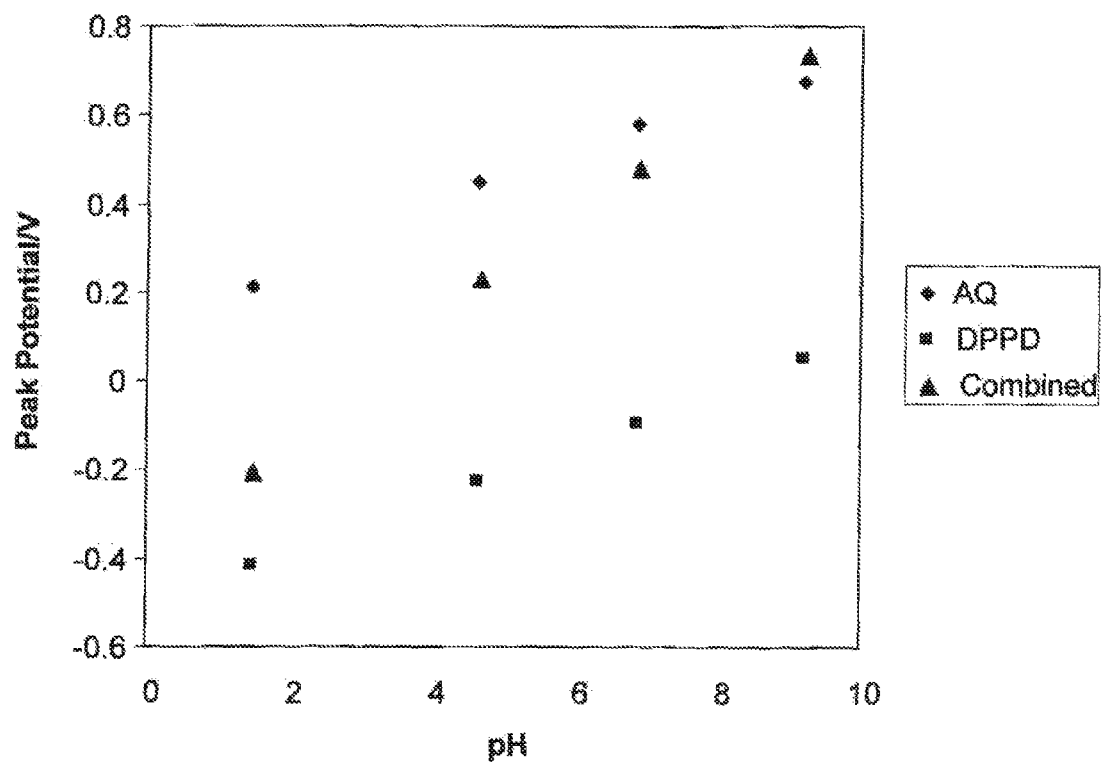
FIG. 7A illustrates the shift of the peak potential for anthraquinone, diphenyl-p-phenylenediamine and a combination of the two redox species, in accordance with an embodiment of the present invention.

FIG. 7A depicts the relationship between the redox potential and pH for both the DPPD (■) and AQ (♦). The plot reveals a linear response from pH 4 to 9 with a corresponding gradient of ca 59 mV/pH unit (at 25° C.) which is consistent with an n electron, m proton transfer where n and m are likely to be equal to two. By combining the two individual curves in a manner as described in equation [5], a new function (▲) is derived with a superior sensitivity for the species to be detected.

For the two activated MWCNT species described above, the peak potential using cyclic voltammetry (CV) is found to be pH-dependant. This voltammetric behavior is consistent with previous studies of carbon powder covalently modified with 1-anthraquinonyl groups and can be attributed to the two-electron, two-proton reduction/oxidation of the 1-anthraquinonyl moiety to the corresponding hydroquinone species.

When NB-MWCNTs is studied a more complicated voltammetric pattern can be observed. Upon first scanning in a reductive fashion a large, electrochemically irreversible peak is observed (labeled as system I), the exact peak potential of which depends on the pH studied. When the scan direction is reversed and swept in an oxidative fashion a new peak at more positive potentials than the irreversible peak is observed; which upon repeat cycling was found to behave in an electrochemically reversible fashion as the corresponding reduction wave was observed. This system is labeled as system II.

Again the exact peak potential of system II is found to vary with the pH studied. This behavior is consistent with the reduction mechanism of the nitro moiety in aqueous media as exemplified by nitrobenzene in FIG. 4D. It is worth noting that all subsequent characterization procedures for NB-MWCNTs are carried out on system II, which corresponds to the reversible arylnitroso/arylhydroxylamine couple, after several initial scans are performed to form this redox couple.

When investigating the effect of pH of AQ-MWCNTs and NB-MWCNTs over the range pH 1.0 to pH 12.0 using CV and square wave voltammetry (SWV) at room temperature as well as the behavior of AQ-MWCNTs at elevated temperatures up to 70° C. SWV was used because it provides us with a sharp, well-defined peak in a single sweep. As concomitant proton loss/gain occurs on oxidation/reduction of AQ-MWCNTs or NB-MWCNTs (see FIGS. 4C and 4D respectively) the peak potential depends on the local proton concentration, i.e. pH, as described by the Nernst equation [6]:

$$E_{peak} = E^0_{formal} - \frac{2.3RTm}{nF}pH \quad [6]$$

where m and n, the number of protons and electrons transferred respectively, are both likely to be equal to two in the case of AQ-MWCNTs and the arylnitroso/arylhydroxylamine couple in the case of NB-MWCNTs. The formulation [6] of the Nernst equation is equivalent to those of equations [1] and [2].

Figure 7B:
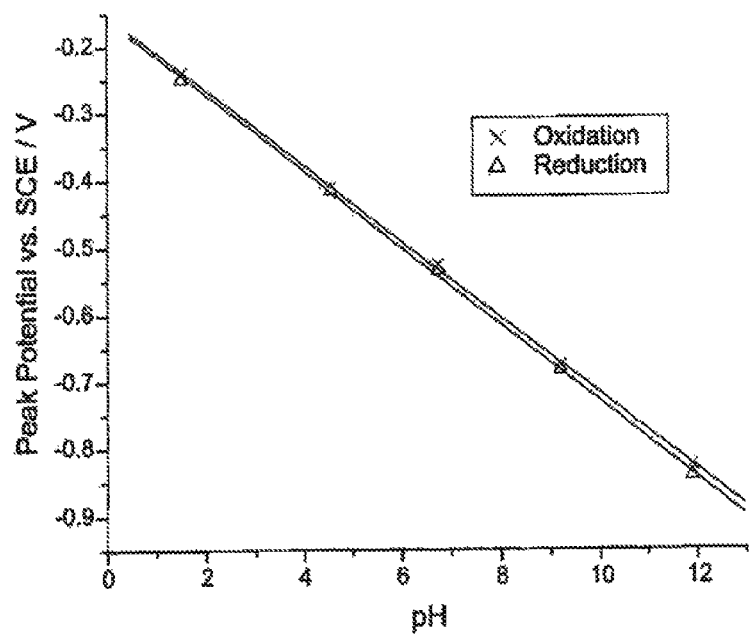
FIGS. 7B-C are plots of peak potential against pH for the redox species of FIGS. 4C and 4D, respectively, over the pH range pH 1.0 to pH 12.0 at 293 K at various conditions, in accordance with an embodiment of the present invention.
Figure 7C:
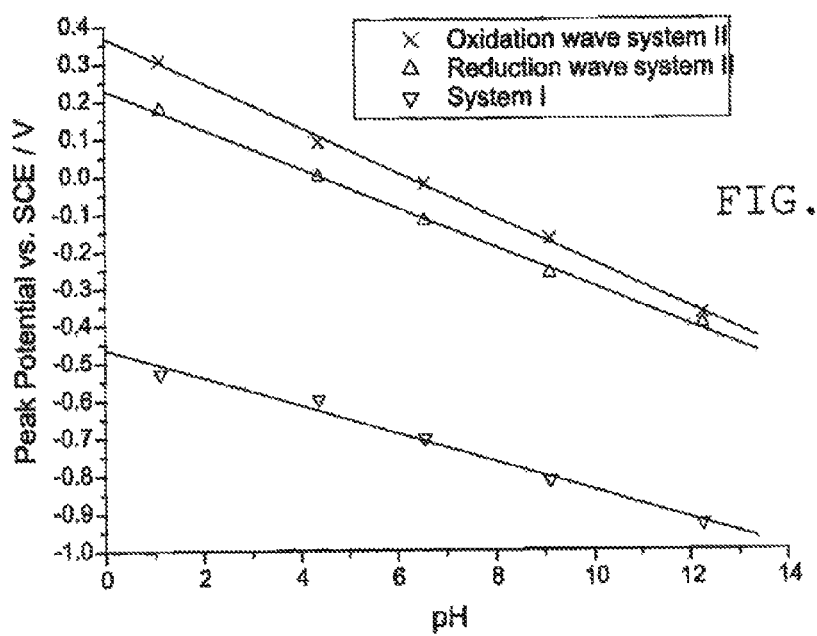

At room temperature the peak potentials for both AQ-MWCNTs and NB-MWCNTs are found to shift to more negative potentials with increasing pH as predicted. A corresponding plot of peak potential against pH was found to be linear over the entire pH range studied in all cases (see FIGS. 7B and 7C, respectively) and a comparison of the gradient of the plots of peak potential versus pH were found to be close to the ideal value of 58.1 mV/pH unit with the exception of the irreversible peak (system I) for NB-MWCNTs which was found to shift by only 37.6 mV/pH unit.

The response of AQ-MWCNTs to pH at elevated temperatures up to 70° C. was studied using SWV. Note that the pH of the solutions used may vary with temperature, and so to this end three IUPAC buffers with a known pH at each temperature studied were employed. These are the pH 4.6, pH 6.8 and pH 9.2 buffers. The Nernst equation predicts that the peak potential should shift to more negative values as the temperature is increased due to the temperature dependence of the formal potential ($E^0_{peak}$).

FIG. 7D does indeed reveal that as the temperature is increased the peak potential is shifted to more negative values. However, in contrast to the behavior of carbon powder covalently derivatised with the anthraquinonyl moiety (AQ-carbon), where the peak currents increase steadily with increasing temperature after an initial increase in peak current up to ca 40° C., the peak currents for AQ-MWCNTs gradually decreases with increasing temperature. This behavior has also been previously observed for MWCNT agglomerates at elevated temperatures. The temperature invariance of derivatised MWCNTs is not fully understood, but has a potential advantage for pH sensors according to some embodiments of the present invention, which are required for use in elevated temperature environments.

In FIG. 7E there is illustrated the effect of varying pH at room temperature for molecular anthraquinone in the solution phase versus the AQ-MWCNTs immobilized onto a bppg electrode. One (1) mM anthraquinone solutions are prepared at each pH and studied using cyclic voltammetry at a bare bppg electrode. The variation of peak potential with pH for both cases over the pH range 1.0 to 14.0 are studied with additional experiments carried out at pH 10.5, pH 13.0 and pH 14.0. The plot of peak potential versus pH for both 1 mM anthraquinone in solution and for the immobilized AQ-MWCNTs reveals that, in the case of AQ-MWCNTs, a linear response is observed over the entire pH range studied.

However for the anthraquinone in the solution phase, the plot is no longer linear above ca. pH 10.5 (FIG. 7E). This can be attributed to the pKa for the removal of the first proton, $pKa_1$, of the reduced form of anthraquinone (see FIG. 4C) in solution being ca. $pKa_1=10$. The pKa for the removal of the second proton is ca $pKa_2=12$. At higher pHs than pH 10 the reduced form of anthraquinone may be deprotonated causing a change in the variation of peak potential with pH. No such deviation from linearity is observed for the AQ-MWCNTs. From this it may be concluded that derivatization onto the surface of the MWCNTs may change the $pK_a$ of the anthraquinonyl moiety. This demonstrates that derivatization onto MWCNTs may prove advantageous to the analytical sensing of pH as the pH window for use is favorably widened for derivatised AQ-MWCNTs compared to free anthraquinone in solution.

Analysis of the peak potential as a function of pH at each temperature shows good agreement between the experimental and theoretically predicted values thereby showing the mechanism can be readily used as a simple, inexpensive pH electrochemical sensor, which sensor works over a wide range of temperatures. Merely by way of example, the novel sensor may be placed inside various wellbore tools and installations as described in the following examples.

Figure 8:
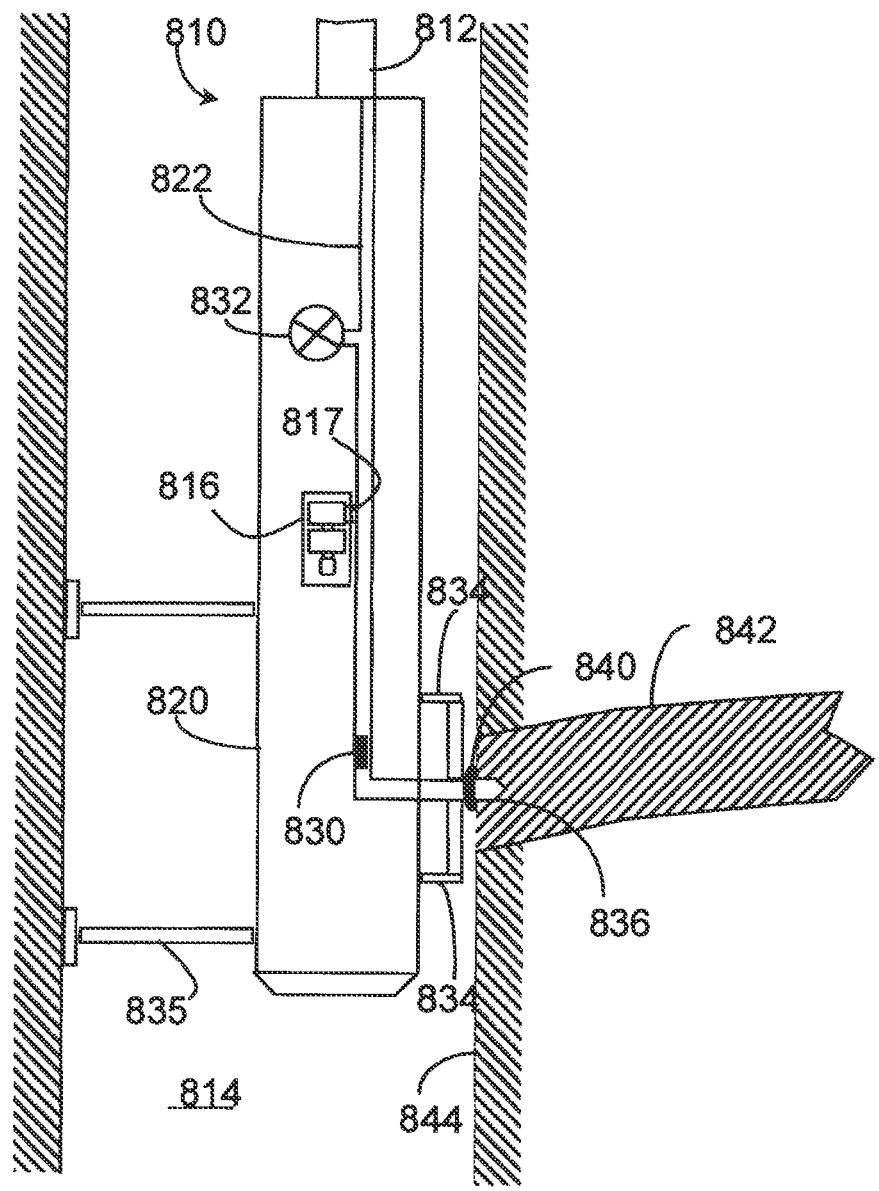
FIG. 8 illustrates an example of an electrochemical sensor, in accordance with an embodiment of the present invention, as part of a wireline formation testing apparatus in a wellbore.
Figure 9:
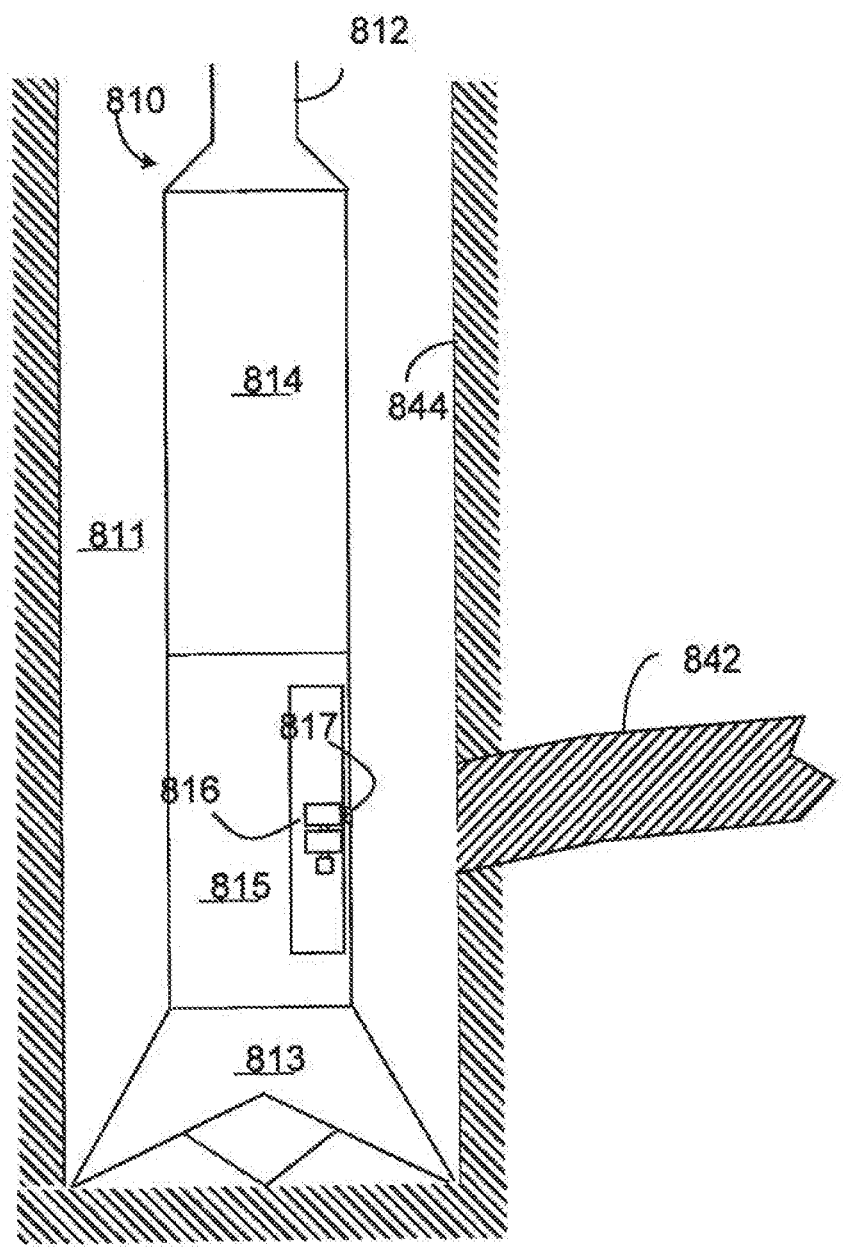
FIG. 9 shows a wellbore and the lower part of a drill string including the bottom-hole-assembly, with a sensor in accordance with the invention.
Figure 10:
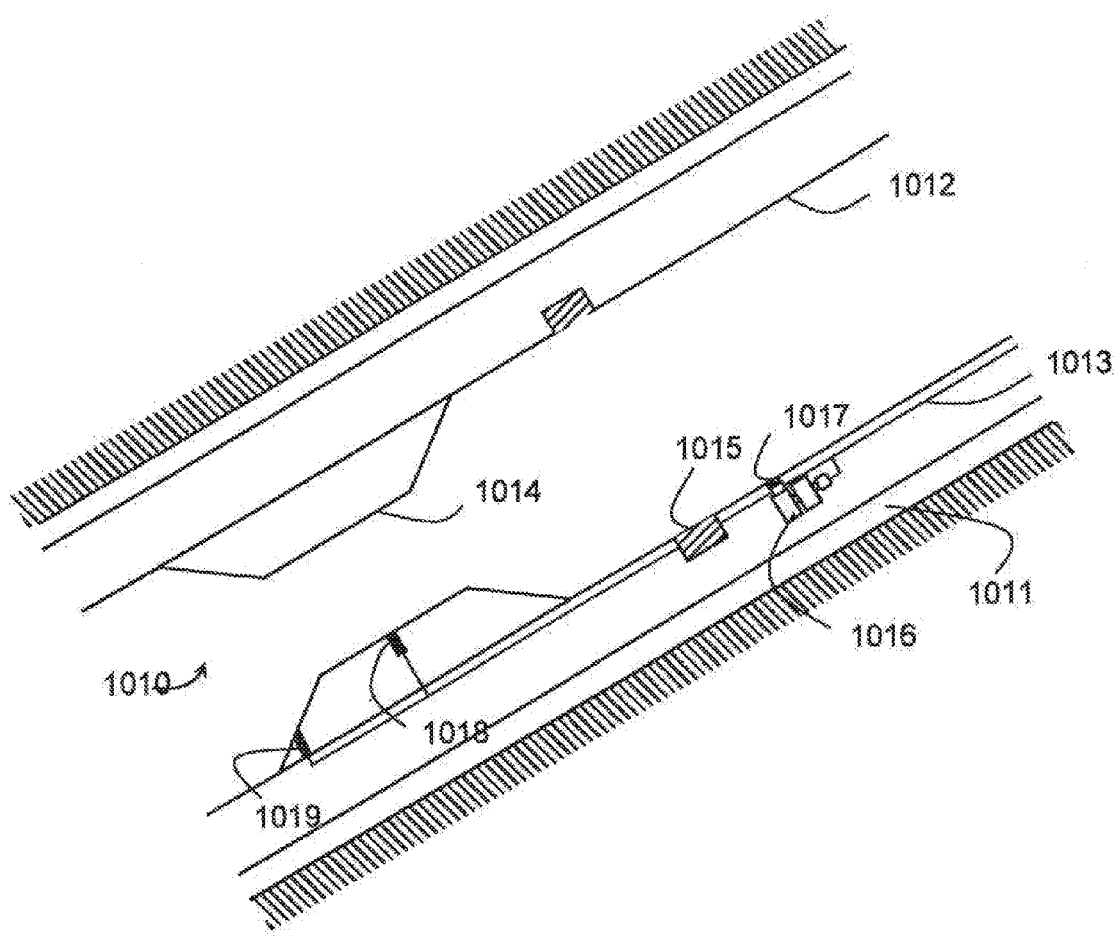
FIG. 10 shows a sensor located downstream of a venturi-type flowmeter, in accordance with the invention.

In FIGS. 8-10 the sensor is shown in various possible downhole applications. In FIG. 8, there is shown a formation testing apparatus 810 held on a wireline 812 within a wellbore

814. The apparatus 810 is a well-known modular dynamic tester (MDT, Mark of Schlumberger) as described in the co-owned U.S. Pat. No. 3,859,851 to Urbanosky, U.S. Pat. No. 3,780,575 to Urbanosky and U.S. Pat. No. 4,994,671 to Safinya et al., with this known tester being modified by introduction of a electrochemical analyzing sensor 816 as described in detail above (FIG. 8). The modular dynamics tester comprises body 820 approximately 30 m long and containing a main flowline bus or conduit 822. The analysing tool 816 communicates with the flowline 822 via opening 817. In addition to the novel sensor system 816, the testing apparatus comprises an optical fluid analyser 830 within the lower part of the flowline 822. The flow through the flowline 822 is driven by means of a pump 832 located towards the upper end of the flowline 822. Hydraulic arms 834 and counterarms 835 are attached external to the body 820 and carry a sample probe tip 836 for sampling fluid. The base of the probing tip 836 is isolated from the wellbore 814 by an o-ring 840, or other sealing devices, e.g. packers.

Before completion of a well, the modular dynamics tester is lowered into the well on the wireline 812. After reaching a target depth, i.e., the layer 842 of the formation which is to be sampled, the hydraulic arms 834 are extended to engage the sample probe tip 836 with the formation. The o-ring 840 at the base of the sample probe 836 forms a seal between the side of the wellbore 844 and the formation 842 into which the probe 836 is inserted and prevents the sample probe 136 from acquiring fluid directly from the borehole 814.

Once the sample probe 836 is inserted into the formation 842, an electrical signal is passed down the wireline 812 from the surface so as to start the pump 832 and the sensor systems 816 and 830 to begin sampling of a sample of fluid from the formation 842. The electrochemical detector 816 is adapted to measure the pH and ion-content of the formation effluent.

A bottle (not shown) within the MDT tool may be filled initially with a calibration solution to ensure in-situ (downhole) calibration of sensors. The MDT module may also contain a tank with a greater volume of calibration solution and/or of cleaning solution which may periodically be pumped through the sensor volume for cleaning and re-calibration purposes.

Electrochemical probes in an MDT-type downhole tool may be used for the absolute measurements of downhole parameters which significantly differ from those measured in samples on the surface (such as pH, Eh, dissolved $H_2S$, $CO_2$). This correction of surface values is important for water chemistry model validation.

A further possible application of the novel sensor and separation system is in the field of measurement-while-drilling (MWD). The principle of MWD measurements is known and disclosed in a vast amount of literature, including for example U.S. Pat. No. 5,445,228, entitled "Method and apparatus for formation sampling during the drilling of a hydrocarbon well".

In FIG. 9, there is shown a wellbore 911 and the lower part of a drill string 912 including the bottom-hole-assembly (BHA) 910. The BHA carries at its apex the drill bit 913. It includes further drill collars that are used to mount additional equipment such as a telemetry sub 914 and a sensor sub 915. The telemetry sub provides a telemetry link to the surface, for example via mud-pulse telemetry. The sensor sub includes the novel electrochemical analyzing unit 916 as described above. The analyzing unit 916 collects fluids from the wellbore via a small recess 917 protected from debris and other particles by a metal mesh.

During drilling operation wellbore fluid enters the recess 917 and is subsequently analyzed using sensor unit 916. The results are transmitted from the data acquisition unit to the telemetry unit 914, converted into telemetry signals and transmitted to the surface.

A third application is illustrated in FIG. 10. It shows a Venturi-type flowmeter 1010, as well known in the industry and described for example in the U.S. Pat. No. 5,736,650. Mounted on production tubing or casing 1012, the flowmeter is installed at a location within the well 1011 with a wired connection 1013 to the surface following known procedures as disclosed for example in the U.S. Pat. No. 5,829,520.

The flowmeter consists essentially of a constriction or throat 1014 and two pressure taps 1018, 1019 located conventionally at the entrance and the position of maximum constriction, respectively. Usually the Venturi flowmeter is combined with a densitometer 1015 located further up- or downstream.

The electrochemical analyzing unit 1016 is preferably located downstream from the Venturi to take advantage of the mixing effect the Venturi has on the flow. A recess 1017 protected by a metal mesh provides an inlet to the unit.

During production wellbore fluid enters the recess 1017 and is subsequently analyzed using sensor unit 1016. The results are transmitted from the data acquisition unit to the surface via wires 1013.

A further possible application for an embodiment of the present invention is in production logging. In order to determine the producing zones of a well, the well is traversed using a logging tool. For vertical and near vertical wells, the tool is allowed to move under gravity, controlled by a cable from the wellhead. For highly deviated wells, the tool is pushed/pulled using either coiled tubing from the surface, or a tractor powered via a cable from the surface.

A typical tool string comprises sensors for taking a series of measurements aimed at determining the flow distribution in the well, in terms of phase fractions and position. Measurements include spinners to determine a local velocity (distribution), and fluid fraction measurement probes—for example electrical or optical probes. These measurements are often used in combination in order to maximize the information gained from each pass of the well.

In certain aspects, a pH sensor according to an embodiment of the present invention, may be mounted onto this tool, and used to measure pH along a well. The pH of the aqueous phase may be determined by its composition, temperature and pressure and may reveal information on the influx of fluids into the well as well as the movement of fluids within the reservoir.

As well as revealing information on fluid influxes and flows within the reservoir, the pH measurement may also be used to assess those parts of the production system that are being exposed to high concentrations of acid gases (for which the associated aqueous phase will have a low pH—typically less than about a pH of 4), and are thus prone to corrosion. In certain aspects, this information may be used to determine the strategy for minimizing and/or mitigating corrosion, e.g. through the selective placement of corrosion inhibitors. U.S. Pat. No. 6,451,603 to G. M. Oddie describes how sensors might be incorporated within the blades of the spinners within a production logging tool and is hereby incorporated by reference in its entirety for all purposes.

In certain aspects, a sensor in accordance with an embodiment of the present invention may be incorporated within the blades of the spinners of a production and may provide for increasing mass transfer to the surface of the sensor.

In another aspect, a sensor in accordance with an embodiment of the present invention may be used in the monitoring of fluids pumped into a well for the purposes of fracturing, matrix treatments such as acidizing, or treatments for wellbore consolidation. pH is an important parameter that controls the property of some of these fluids, and monitoring its value may provide a means of assuring the quality of the treatment, particularly where fluids may be blended in surface modules, prior to being pumped downhole.

In addition to using surface monitoring for pumping fluids into a well, pH might be monitored, in accordance with an embodiment of the present invention, on the returns, when a well is brought back on production following the pumping of a treatment fluid. With the contrast in pH between a treatment fluid and the reservoir fluids, the efficacy of the treatment, and the placement of the treatment fluids, may be assessed.

In yet further aspects, a pH sensor, in accordance with an embodiment of the present invention, may be mounted on surface pumping units or blenders, or form part of a separate monitoring module, placed in-line and/or the like. In still further aspects, a sensor in accordance with an embodiment of the present invention may be deployed downhole on a coiled tubing unit, where the coiled tubing may be used to convey fluids downhole, and where the pH sensor may be located at the coiled tubing head, or as part of a measurement sub conveyed by the coiled tubing unit, and provide information on the state of the fluids downhole.

Another application of an embodiment of the present invention may be in the monitoring of underground bodies of water for the purposes of resource management. From monitoring wells drilled into the aquifers, one or more sensors, in accordance with an embodiment of the present invention, may be deployed on a cable from the surface—either for short duration (as part of a logging operation) or longer term (as part of a monitoring application). In certain aspects of the present invention, a pH sensor, in accordance with an embodiment of the present invention, may be used in the monitoring of aquifers, where long term unattended monitoring of pH is required, e.g. in the monitoring of shallow groundwater on top of $CO_2$ storage, where the pH in the shallow groundwater may indicate whether $CO_2$, injected into a deeper aquifer for the purposes of $CO_2$ sequestration, is escaping to the surface. The pH sensor may be interfaced with a data-logger and the measurements from the sensor stored for later retrieval, may be transmitted to surface for direct analysis and/or the like.

In addition, in certain aspects, the deployment of the pH sensor within producing wells on a cable may provide information on produced water quality. In further aspects, the pH sensor may be deployed in injection wells, e.g. when water is injected into an aquifer for later retrieval, where pH may be used to monitor the quality of the water being injected or retrieved.

There may be a significant heterogeneity in the composition, and hence the pH, of waters produced from a reservoir: reflecting both the vertical and horizontal variations that exist in rock and fluid composition. These variations may arise from natural processes during the formation of a basin or may come about through the injection of fluids to improve oil recovery, e.g., $CO_2$, surface waters or treatment fluids. Monitoring pH using an embodiment of the present invention beyond the wellhead in surface or subsea pipelines may provide information on the nature of the flow within a reservoir—providing information on events such as water breakthrough or the like—and/or may give warning when corrosion may become an issue because of abnormally low pH that may be due to un-reacted acid treatments returning to surface or because of the natural production of the acid gases $H2S$ or $CO2$. A pH sensor in accordance with an embodiment of the present invention may be deployed beyond the wellhead, permanently or temporarily, within pipelines, or located at the manifolds where pipeline flows are brought together or divided.

In wells where reservoir pressures are insufficient, electro-submersible pumps ("ESPs") can be deployed within the well to increase production. These pumps are deployed from surface with a power cable and fluid injection lines. In certain aspects of the present invention, a pH sensor in accordance with an embodiment of the present invention may be deployed permanently on the ESP and may provide pH information that may be used to interpret fluid composition. In such aspects, the sensor may provide warning of potential materials failure from acid corrosion or the like. In addition to this application, alternative means of deployment of a sensor in accordance with an embodiment of the present invention may be within a permanent monitoring system, may be a part of a completion of a well and/or the sensors may be deployed through a casing of the wellbore to monitor the fluids outside of the casing, e.g. in assessing zonal isolation or the like.

While the preceding describe uses of the electrochemical sensor in the hydrocarbon and water industries, embodiments of the present invention may provide an electrochemical sensor for detecting an analyte in a whole host of industries, including food processing, pharmaceutical, medical, water management and treatment, biochemistry, research laboratories and/or the like. Merely by way of example, one embodiment of the present invention provides an electrochemical sensor comprising a polymer coating where the coating may prevent diffusion of a redox species from the working electrode, but still allow for interactions between an analyte and one or more of the redox species disposed on the working electrode.

Figure 11:
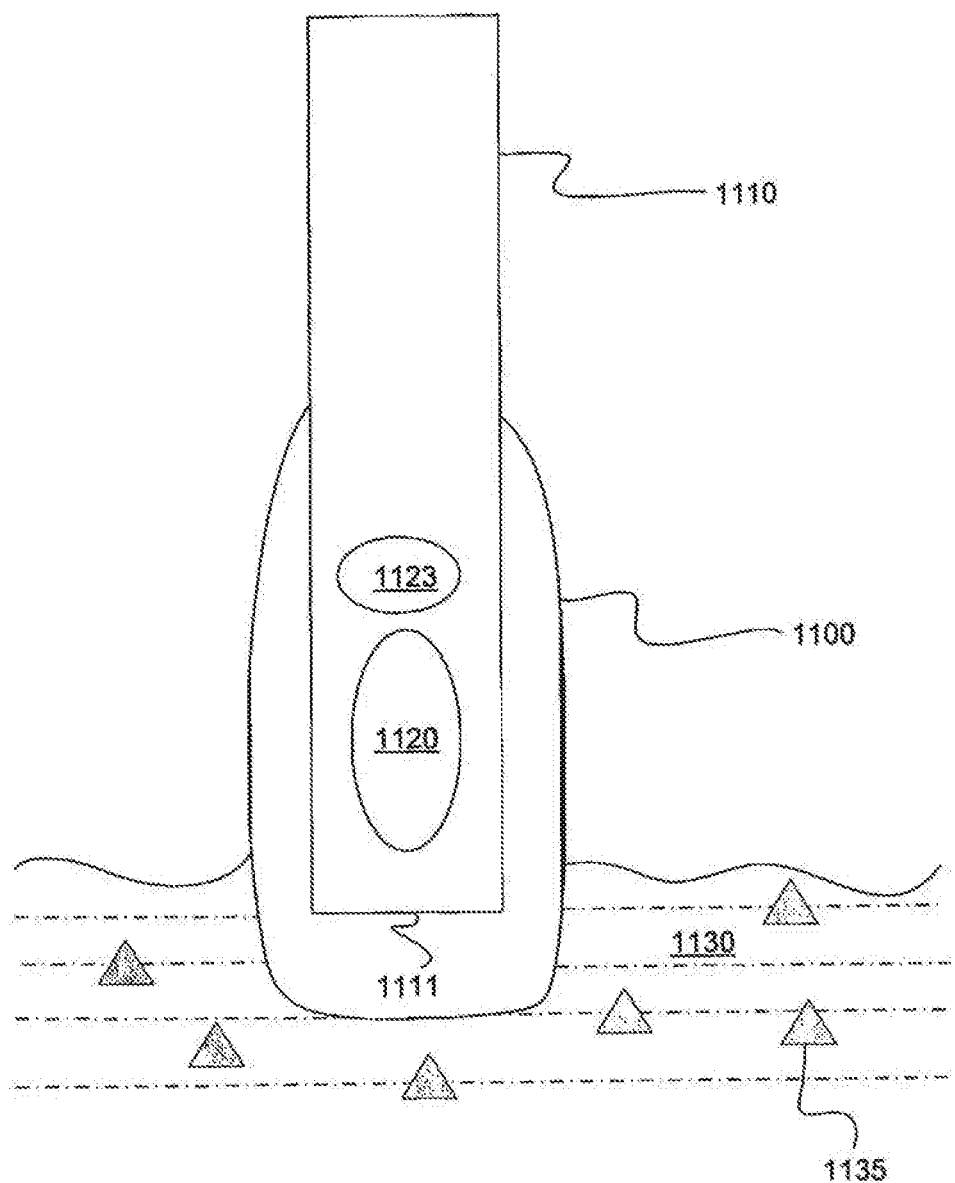
FIG. 11 illustrates a working electrode covered at least in part by a polymer layer, in accordance with an embodiment of the present invention.

FIG. 11 is a schematic-type representation of a working electrode with polymer coating covering at least a portion of the working electrode, in accordance with one embodiment of the present invention. In an embodiment of the present invention, a polymer coating 1100 may be applied to a working electrode 1110 that is coupled with/comprises a sensitive redox species 1120; where the sensitive redox species 1120 is sensitive to an analyte 1135 to be detected. The analyte 1135 may be found in a fluid 1130, where the fluid 1130 may be a fluid that is being tested or the fluid 1130 may comprise a fluid into which the analyte is deposited/diffused, for example by diffusion from a sample flowing over a membrane (not shown) contacting the fluid 1130. In some aspects, the fluid 1130 may comprise a buffer solution.

The polymer coating 1100 may be configured to prevent leeching, diffusion and/or the like of the sensitive redox species 1120 into the fluid 1130. This may be important where the fluid 1130 is a fluid being tested and it is not desirable to contaminate the fluid 1130, for example the fluid may be water in a water treatment process, a batch of a pharmaceutical process, a food substance or the like. In other aspects, the electrochemical sensor/working electrode may be subject to human contact in use and it may be desirable to prevent such contact with the redox species.

Furthermore, the application of the polymer coating 1100 to the working electrode 1110 may serve to anchor the redox species to the working electrode 1110. As such, methods of fabrication of the working electrode may be used wherein the redox species is not chemically coupled to the working electrode 1110.

In an embodiment of the present invention, the working electrode may comprise both the sensitive redox species 1120 and as insensitive redox species 1123. In such an embodiment, the polymer coating 1100 may be configured to prevent leeching, diffusion and/or the like of either the sensitive redox species 1120 and/or the insensitive redox species 1123. Merely by way of example, in practice, the insensitive redox species 1123 is often the most problematic of the redox species to anchor to the working electrode 1110. This may be because of the properties of the insensitive redox species 1123 and/or the method of depositing the insensitive redox species 1123 on the working electrode 1110 or binding the insensitive redox species 1123 to the working electrode 1110.

To work effectively, the polymer coating 1100 should act to prevent leeching, diffusion, movement and/or the like of the insensitive redox species 1123 and/or the sensitive redox species 1120 from the working electrode to the fluid 1130. At the same time, the polymer coating 1100 should allow the fluid 1130 and/or the analyte 1135 to permeate, diffuse to, come into contact with, perturb and/or the like the sensitive redox species 1120 on the working electrode 1110.

Merely by way of example, in one embodiment of the present invention, the polymer coating 1100 may comprise a polysulphone polymer and in another embodiment, the polymer coating 1100 may comprise a polystyrene polymer. As persons of skill in the art may appreciate, other polymers may be used in accordance with an embodiment of the present invention provided the polymers do not interfere with the operation of the sensor.

In experiments using small amounts of polymer coated on the working electrode 1110, it was found from a plot of peak current against pH that there was steady decrease in peak current with time. This decrease in current is due to a redox species on the working electrode 1110 diffusing through the polymer coating 1100 into the fluid 1130. The redox species may be the sensitive redox species 1120 or the insensitive redox species 1123 that is coupled with the working electrode 1110. For example, the non-sensitive redox species 1123, which may comprise ferrocene or the like, may be attached to the working electrode 1110 to provide a reference that may be used to provide for peak-to-peak measurements of the redox peaks produced by the sensitive redox species 1120 and the insensitive redox species 1123. As noted above, in such aspects, the electrochemical sensor effectively has two reference electrodes. The processor may process a measurement of the analyte using the peak-to-peak separation of the redox peaks produced by the sensitive redox species 1120 and the insensitive redox species 1123.

Merely, by way of example, Applicants determined that low concentrations/low amounts of polymer are insufficient to prevent diffusion of the sensitive redox species 1120 and/or the insensitive redox species 1123 from the working electrode 1110 into the fluid being 1130. However, applicants found that an increased concentration of polymer may provide for effective operation of the electrochemical sensor and decreased diffusion of the sensitive redox species 1120 and/or the insensitive redox species 1123 into the fluid 1130. Furthermore, in certain aspects of the present invention, it may be easier or more efficient to bind/hold the sensitive redox species 1120 and/or the insensitive redox species 1123 to the working electrode 1110 when the polymer coating 1100 is present. In such aspects, the polymer layer 1100 may be configured with a consideration of retaining the sensitive redox species 1120 and/or insensitive redox species 1123 at the working electrode 1110 and/or ease of manufacturing the working electrode 1110.

Merely by way of example, in certain aspects, using a macro-electrode, of the order of 1 to 5 mm in diameter, the polymer layer 1100 may comprise 1000 micrograms of the polymer disposed over the working electrode 1110. However, such a large amount of the polymer may reduce the reaction time of the electrochemical sensor as it may take up to several hours for the fluid 1130 to diffuse through the polymer layer 1100 and interact with the working electrode 1110.

In some aspects, the sensitive redox species 1120 and/or the insensitive redox species 1123 may be disposed on a tip 1111 of the working electrode 1110 and the polymer layer 1100 may cover at least the tip 1111 of the working electrode 1110. In other aspects, the sensitive redox species 1120 and/or the insensitive redox species 1123 may cover an area or areas, which may be referred to as active areas, of the working electrode 1110 and the polymer layer 1100 may coat the active area(s). In other aspects, the working electrode 1110 may be coupled with a redox species and then covered with the polymer.

In one embodiment of the present invention, the concentration, amount and/or thickness of the polymer coating 1100 may be configured to provide for preventing contamination of the fluid 1130 and/or loss of the sensitive redox species 1120 and/or the insensitive redox species 1123 from the working electrode 1110 as well as for allowing diffusion of the analyte 1135 to the sensitive redox species 1120. In some embodiments, a working electrode of diameter less than 10 mm may be coated with over a thousand micrograms of polymer. In such an embodiment, it may take of the order of several hours for the analyte 1135 to overcome the polymer layer 1100 and interact with the sensitive redox species 1120. In certain aspects, where a response time of less than a matter of hours are required, less than 1000 micrograms of polymer may be used to coat a working electrode with a diameter of the order of 1-5 mm.

To produce an electrochemical sensor with a response time of the order of minutes or seconds with electrodes having diameters between 1-5 mm less than 500 micrograms of polymer may be used. Of course, the characteristics of the polymer chosen for the polymer coating 1100 will also affect the amount to be used. Merely by way of example, for a working electrode with a diameter between 1 and 5 mm, to produce a real-time response time and/or a response time of the order of seconds, about 200-400 micrograms of polystyrene may be deposited on the working electrode 1110 or about 10-400 micrograms of polysulfone may be deposited on the working electrode 1110.

To deposit the polymer in a generally uniform layer over the working electrode 1110, the polymer may be spin coated onto the working electrode 1110, dip coated onto the working electrode 1110, applied using solvent evaporation onto the working electrode 1110 and/or the like. In certain aspects, a screen printing process may be used to apply the sensitive redox species 1120, the insensitive redox species 1123 and/or the polymer coating 1100 to the working electrode 1110.

For example, for a solvent evaporation application of the sensitive redox species 1120 and/or the insensitive redox species 1123 to the working electrode 1110, the polymer may be dissolved in a solvent such as dichloromethane ("DCM") or the like. In some embodiments, a concentration/amount of the polymer layer 1100 applied on top of the working electrode 1110 is of the order of tens of milligrams of polymer in about 1-50 milliliters of solution. In other embodiments, a concentration/amount of the polymer layer 1100 applied on top of the working electrode 1110 is of the order of 5-50 of milligrams of polymer in about 1-20 milliliters of solution. In other embodiments, a concentration/amount of the polymer layer 1100 applied on top of the working electrode is of the order of 20-40 of milligrams of polymer in about 1-10 milliliters of solution. In one embodiment of the present invention, the working electrode 110 is coated with 25-35 mg of polymer dissolved in 2 ml of DCM and the DCM is then evaporated to leave a polymer layer on the working electrode 1110 comprising 25-35 micrograms of polymer.

In other embodiments of the present invention, the working electrode 1110 may comprise a micro-electrode. For such embodiments, the amount of polymer used to coat the microelectrode may be between 1-10 micrograms or less than 1 microgram of the polymer. In such configurations, techniques associated with micro-fabrication may be used to apply the polymer to the micro-electrodes. In further embodiments, electrodes of the order of 10 s of millimeters may be used and coatings of more than 600 micrograms or 1000 micrograms of polymer may be used to provide electrochemical sensors with a good response time.

In an embodiment using carbon paste electrodes containing ferrocene as the insensitive redox species 1123 and a polymer layer of polysulphone, an increased voltammetric response was found for pH levels 4, 7 and 9. These findings show the efficiency of the polymer layer in preventing diffusion of ferrocene into the solution since, without the polymer layer, the voltammetric response decreases as a function of time as the ferrocene ions escape into the solution.

A sensor using carbon paste electrodes containing anthraquinone with a polysulphone layer showed increased voltammetric response at pH 4 and 7. Without the polymer, an overall decrease in voltammetric response was found as the active species diffuse into the solution.

The carbon paste electrodes containing ferrocene and anthraquinone species with a polysulphone layer showed initial increase in oxidative waves for both species followed by a decrease at pH 4, fluctuations as pH 7 and an increase at pH 9. The anthraquinone peak is lost before the ferrocene peak suggesting the instability of the former species. In general, Applicants have found that use of a polymer layer over the electrode of the sensor system can prevent or limit diffusion of the redox species—anthraquinone, ferrocene or the like—from the sensor's electrode and by using the correct polymer layer properties still allow for interaction between the redox species and the fluid being tested. As such, a polymer coated electrochemical sensor may be used without causing contamination of the fluid, loss of the redox species and/or the like.

Figure 12:
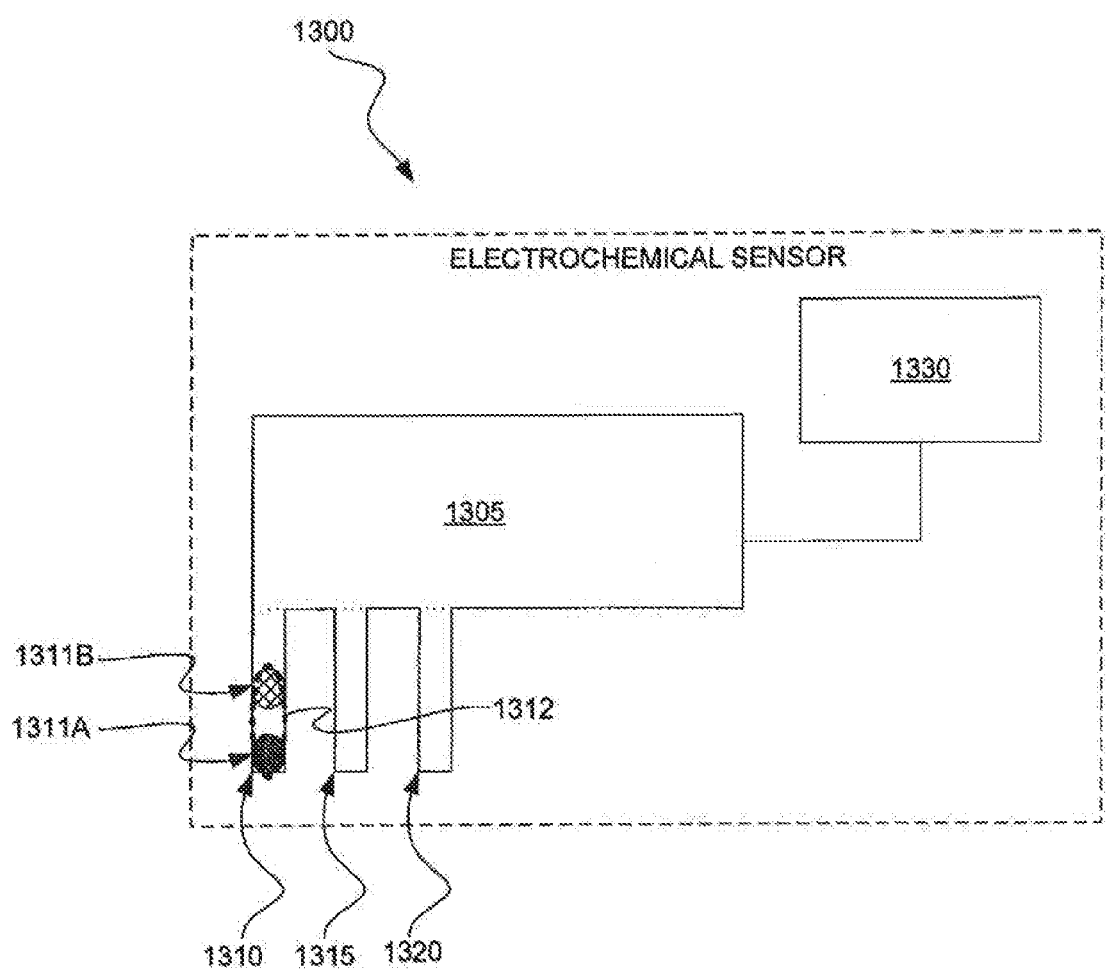
FIG. 12 is a schematic-type representation of an electrochemical sensor, in accordance with an embodiment of the present invention.
Figure 13:
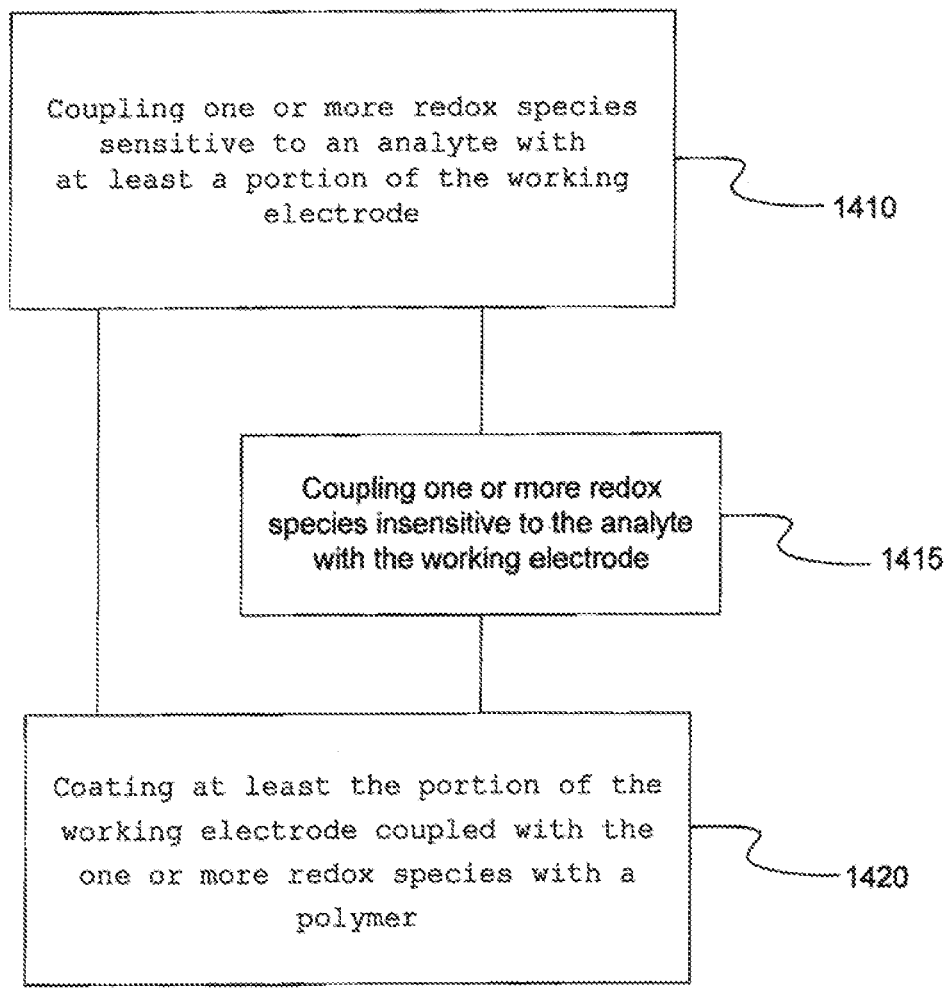
FIG. 13 is a flow-type description of a method for manufacturing a working electrode for an electrochemical sensor, in accordance with an embodiment of the present invention In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 12 is a schematic-type illustration of an electrochemical sensing system in accordance with an embodiment of the present invention. As depicted the electrochemical sensing system 1300 comprises an electrical hardware system 1305. The electrical hardware system 1305 is coupled with one or more electrodes for contacting with a fluid (not shown) to detect/measure a certain analyte.

In some embodiments, the electrodes are contacted directly with a fluid to be analyzed. In other embodiments, the electrodes are contacted with a selected fluid and the fluid to be analyzed may be contacted with a membrane and the analyte to be detected/measured may diffuse through the membrane from the fluid to be analyzed to the selected fluid and it may then be detected/measured by the electrochemical sensor 1300 via the electrodes. In one embodiment of the present invention the electrical hardware system 1305 is electrically coupled with a working electrode 1310, a counter electrode 1315 and a reference electrode 1320.

The electrical hardware system 1305 may comprise a power supply, voltage supply, potentiostat and/or the like for applying an electrical potential to the working electrode 1310, a detector—such as a voltmeter, a potentiometer, a potentiostat, an oscilloscope, an ammeter, resistometer and/or the like—for measuring a potential between the working electrode 1310 and the counter electrode 1315 and/or the reference electrode 1320 and for measuring a current flowing between the working electrode 1310 and the counter electrode 1315 (where the current flow will change as a result of the oxidation/reduction of a sensitive redox species 1311A and/or an insensitive redox species 1311B) and circuitry for electronically coupling the voltage supply or the like, the working electrode 1310, the counter electrode 1315, the reference electrode 1320 and the detector.

In an embodiment of the present invention the electrical hardware system 1305 may sweep a voltage difference across the electrodes and as such the hardware system 1305 may comprise hardware configured for voltammetry so that, for example, linear sweep voltammetry, square wave voltammetry and/or the like may be used to obtain measurements of the analyte using the electrochemical sensor. The electrical hardware system 1305 may include signal processing electronics and the like.

In some embodiments of the present invention, the electrochemical sensing system 1300 comprises at least the working electrode 1310, the counter electrode 1315 and the reference electrode 1320. Such embodiments allow for the use of electrodes that are larger in size than microelectrodes. For example in some embodiments of the present invention the working electrode 1310 may be larger than 1 micro-meter in dimension. In other embodiments the working electrode 1310 may be of the order of 10 s of micro-meters or 100 s of micrometers in dimension. In yet other embodiments the working electrode 1310 may be of the order of millimeters, 10 s of millimeters, centimeters or larger in dimension. Using an electrode that is larger than a microelectrode may reduce/prevent fouling of the electrode or the like.

In one embodiment of the present invention, the working electrode 1310 is coupled with the sensitive redox species 1311A. In certain aspects, the sensitive redox species 1311A comprises a redox species that is sensitive to an analyte to be detected, monitored, measured and/or the like. In an embodiment of the present invention, the insensitive redox species 1311B is coupled with the working electrode 1310. In certain aspects, the insensitive redox species 1311B comprises a redox species that is insensitive to an analyte to be detected, monitored, measured and/or the like.

The area(s) of the working electrode 1310 comprising the sensitive redox species 1311A and the insensitive redox species 1311B may be considered as an active area(s) 1312 of the working electrode 1310. The active area 1312 may be contacted with a fluid to detect/measure the presence of an analyte of interest. In certain aspects, the active area may be covered with a polymer layer/coating or the like to separate the sensitive redox species 1311A and/or the insensitive redox species 1311B from the fluid. In some aspects, the active area 1312 may comprise areas/sections of the working electrode 1310 that are not coupled with the sensitive redox species 1311A and/or the insensitive redox species 1311B.

In an embodiment of the present invention, a voltammetric measurement is made between the working electrode 1310, the counter electrode 1315 and/or the reference electrode 1320. The voltammetric measurement may comprise a current flowing between the working electrode 1310 and the counter electrode 1315, a potential difference between the working electrode 1310 and the counter electrode 1315 and/or a potential difference between the working electrode 1310 and the reference electrode 1320. Such a voltammetric measurement may in some aspects comprise a voltammogram, a square wave volytammogram and or the like. In one embodiment of the present invention, the voltametric response of the electrochemical sensing system 1300 in the presence of an analyte may be output to a processor 1330 for processing.

The reference electrode 1320 may provide the potential against which the potential of the working electrode is compared. This buffering against potential changes is achieved by the electrode containing a constant composition of both forms of its redox couple. In an ideal case the reference potential would be independent of sample composition as the electrode itself is isolated from the sample species through an intermediate bridge. However, this cannot always be achieved as factors such as electrode arrangement, cost etc. have to be considered and hence the reference electrode potential may drift or vary from sample to sample. Because of this drift, among other reasons, in an embodiment of the present invention, the non-sensitive redox species 1311B may be coupled with the working electrode 1310 to provide a reference. In some embodiments of the present invention the reference electrode may comprise silver, silver-chloride and/or the like. In aspects of the present invention the reference electrode is contacted with the fluid.

The processor 1330 may process the voltammetric response to determine the existence of peaks in the response characteristic of oxidation/reduction of the sensitive redox species 1311A, where the peaks are perturbed by the analyte to be detected. In certain embodiments of the present invention, the processor 1330 may process the voltammetric response to determine the existence of peaks in the response characteristic of oxidation/reduction of the insensitive redox species 1311B, unlike the sensitive redox species 1311A, the peaks produced by the insensitive redox species 1311B are not affected by the presence of the analyte. In an embodiment of the present invention, the output peaks from the sensitive redox species 1311A and the insensitive redox species 1311B may be combined and used by the processor to process a measurement of the analyte.

In some embodiments of the present invention, the electrochemical sensing system 1300 may comprise a temperature probe 1325. In certain aspects, the response of the sensitive redox species 1311A to the analyte to be detected and/or the oxidation/reduction characteristics of the insensitive redox species 1311B may be temperature dependant. As such, in an embodiment of the present invention, the temperature of the fluid being tested may be measured by the temperature probe 1325 and communicated to the processor 1330. The processor 1330 may use the temperature to process the detection/measurement of the analyte to be detected from the voltammetric output of the electrochemical sensing system 1300. For example, the processor may calibrate the voltammetric output from the electrochemical sensor 1300 based upon a temperature measurement from the temperature probe 1325.

In certain aspects of the present invention, the sensitive redox species 1311A and insensitive redox species 1311B may be coupled with different working electrodes. In some aspects, the working electrode 1310 may comprise an array of working electrodes. In an embodiment of the present invention, the area of the counter electrode 1315 is of the same order as the area of the working electrode 1310. In other embodiments, the area of the counter electrode 1315 is less than a hundred (100) times the area of the working electrode 1310. In other embodiments the area of the counter electrode 1315 is of the order of between 1 and 90 times the area of the working electrode 1310.

In some embodiments of the present invention, at least the working electrode 1310 may be contacted with the fluid to be tested. As discussed above, in some aspects a polymer layer may be deposited over the working electrode 1310 to prevent the sensitive redox species 1311A and/or the insensitive redox species 1311B diffusing, leeching and/or the like into the fluid being tested. In other aspects, the fluid to be tested is contacted with a membrane that allows for a flow of the analyte to be detected or measured through the membrane into a fluid in contact with at least the working electrode 1310. In this way, the electrochemical sensing system 1300 may be protected from any detrimental properties of the fluid being tested.

FIG. 14 is a flow-type description of a method for manufacturing a working electrode for an electrochemical sensor, in accordance with an embodiment of the present invention. In step 1410 a working electrode is coupled with one or more redox species sensitive to an analyte. The coupling of the redox species to the working electrode may performed using chemical coupling/bonding, chemical reaction, electrical coupling, by deposition onto the working electrode, by binding to the working electrode, by printing (jet printing, screen printing and/or the like) onto the working electrode, by dip coating, by spin coating, by solvent evaporation coating, by electro-deposition and/or the like.

In step 1415, one or more redox species that are insensitive to the analyte may be coupled with the working electrode. The coupling of the redox species to the working electrode may performed using chemical coupling/bonding, chemical reaction, electrical coupling, by deposition onto the working electrode, by binding to the working electrode, by printing (jet printing, screen printing and/or the like) onto the working electrode, by dip coating, by spin coating, by solvent evaporation coating, by electro-deposition and/or the like.

In step 1420, at least a portion of the working electrode is coated with a polymer. The polymer may be applied to the working electrode by dip coating, spin coating, solvent evaporation coating, electro-deposition, chemical reaction, chemical bonding and/or the like. In certain aspects, the entire working electrode is coated with the polymer coating. In another embodiment, one or more active portions of the working electrode may be coated with the polymer, where the active portion(s) may comprise portions of the working electrode on which the sensitive and/or the insensitive redox species are disposed. In some aspects, the working electrode may be disposed in a housing, holder and or the like and the portion of the working electrode extending from the housing, holder and or the like may be considered an active portion of the working electrode for contacting with a fluid. In other aspects, the sensitive and/or the insensitive redox species may be disposed in a recess in the working electrode and the recess may be covered with the polymer.

In an embodiment of the present invention, the working electrode may simply be coated with the redox species, bound to the redox species, have the redox species deposited on its surface in the manufacturing process since the polymer applied in step 1420 may hold the redox species in place so that it is electrically coupled with the working electrode. For example, in an embodiment of the working electrode, in step 1415, the working electrode may be contacted with a solution of the redox species. In another embodiment, the redox species may be coupled with carbon particles, such as carbon nanotubes or the like, and in step 1415 the carbon particles may be deposited on the working electrode or disposed in an indent in the working electrode. The redox species may be solvent cast to the carbon, deposited on the carbon or the like. In other embodiments, the redox species may be mixed with the solvent and the mixture may then be coupled with the working electrode.

Since as mentioned above, it is often the insensitive redox species that is the most problematic to maintain at the working electrode, the polymer layer may be applied to the working electrode to provide for maintaining the insensitive redox species at the working electrode. Merely by way of example, in one embodiment of the present invention, in step 1410 the sensitive redox species may be chemically coupled with the working electrode, in step 1415 the working electrode may be contacted with or have disposed thereon the insensitive redox species and in step 12420 the polymer coating may be applied.

Moreover, in some embodiments of the present invention, the sensitive redox species may be chemically coupled with the working electrode and then the insensitive redox species may be deposited on the working electrode. In this way it is not necessary to chemical bind both the sensitive and the insensitive redox species to the working electrode; which way be problematic, expensive and/or the like. In such, embodiments the application of the polymer layer may serve to stabilize the insensitive redox species at the working electrode. This may provide for ease and economical methods of manufacture of the working electrode.

In some embodiments of the present invention, the sensitive and/or the insensitive redox species may be coupled with the working electrode using a paste, binder and/or the like. For example, the sensitive and/or the insensitive redox species may be in a solid/crystalline form and may be applied to the working electrode in combination with the paste/binder or deposited on the electrode after which the paste/binder is applied. Once the sensitive and/or the insensitive redox species and the paste/binder are applied to the electrode the polymer layer may be applied over the sensitive and/or the insensitive redox species and the paste/binder.

In one embodiment, the sensitive and/or the insensitive redox species may be applied to the working electrode by an inkjet-type process in combination with a binder, such as ink or the like. After application of the sensitive and/or the insensitive redox species by the inkjet-type process a polymer layer may be applied to the working electrode.

In one embodiment of the present invention, the electroactive insensitive redox species may either be attached to, chemically or the like, an electrode surface or be placed on top of or within an electrode structure. In the latter case, the insensitive redox species may be insoluble or have low solubility, in both its oxidized and reduced forms, in the media in which the electrode is to be placed. In an embodiment of the present invention, the insensitive redox species may be formulated to provide that chemical groups are attached to the insensitive redox active species to lowers its solubility.

In one embodiment of the present invention, the working electrode may comprise the sensitive and the insensitive redox species. Merely by way of example, where the sensitive redox species comprises a quinine moiety (Aq) and the insensitive species comprises a ferrocene both AQ and Fc may be chemically bound to a single working/sensing electrode and a polymeric coating may be applied to the working/sensing electrode. In another embodiment, both the AQ and Fc are chemically bound to a single working/sensing electrode surface and a polymeric coating is applied to working/sensing, counter and reference electrodes.

In yet other embodiments, AQ is chemically bound to a single working/sensing electrode and Fc is coated onto the working/sensing electrode and a polymeric coating is applied to only this electrode. Alternatively, AQ is chemically bound to a single working/sensing electrode and Fc is coated onto the working/sensing electrode and a polymeric coating is applied to sensing, counter and reference electrodes.

In one embodiment, AQ is chemically bound to one working/sensing electrode and Fc is coated or bound to a second working/sensing electrode and a polymeric coating is applied to only the Fc coated/bound electrode. In other aspects, AQ is chemically bound to a first working/sensing electrode and Fc is coated or bound to a second working/sensing electrode and a polymeric coating is applied to both the AQ and the Fc coated/bound working/sensing electrodes. In further aspects, AQ is chemically bound to a first working/sensing electrode and Fc is coated or bound to a second working/sensing electrode and a polymeric coating is applied to all electrodes.

Various embodiments and applications of the invention have been described. The descriptions are intended to be illustrative of the present invention. It will be apparent to those skilled in the art that modifications may be made to the invention as described without departing from the scope of the claims set out below.

The invention claimed is:

1. A working electrode for an electrochemical sensor for measuring pH of a fluid, comprising:
   a conducting substrate;
   a first set of redox species coupled with the conducting substrate, wherein the first set of redox species comprises one or more non-polymeric redox species that are sensitive to pH, and wherein the coupling of the first set of redox species with the conducting substrate comprises one of the first set of redox species being chemically coupled with the conducting substrate, the first set of redox species being coated on the conducting substrate and the first set of redox species being deposited on the conducting substrate; and
   a polymer layer which consists of polymer and which directly covers at least an area of the conducting substrate where the conducting substrate is coupled with the first set of redox species so that the polymer layer directly covers the first set of redox species, the polymer layer being configured to allow hydrogen ions to diffuse through the polymer layer to interact with the first set of redox species and to prevent diffusion of the non-polymeric redox species from the working electrode.

2. The working electrode of claim 1, further comprising:
   a second set of non-polymeric redox species disposed between the conducting substrate and the polymer layer, wherein the polymer layer is configured to prevent diffusion of the second set of non-polymeric redox species from the working electrode.

3. The working electrode of claim 2, wherein the second set of redox species is chemically bound to the conducting substrate.

4. The working electrode of claim 1, wherein the working electrode comprises an electrode having a diameter between 1 and 5 millimeters and the polymer layer comprises less than 1000 micrograms of polymer.

5. The working electrode of claim 1, wherein the polymer layer consists of a polystyrene polymer.

6. The working electrode of claim 5, wherein the working electrode has a diameter between 1 and 5 millimeters and the polymer layer consists of less than 600 micrograms of the polystyrene polymer.

7. The working electrode of claim 5, wherein the working electrode has a diameter between 1 and 5 millimeters and the polymer layer consists of between 100 and 500 micrograms of the polystyrene polymer.

8. The electrochemical sensor of claim 1, wherein the polymer layer consists of a polysulphone polymer.

9. The electrochemical sensor of claim 8, wherein the working electrode has a diameter between 1 and 5 millimeters and the polymer layer consists of less than 600 micrograms of the polysulphone polymer.

10. The working electrode of claim 8, wherein the working electrode has a diameter between 1 and 5 millimeters and the polymer layer consists of between 10 and 500 micrograms of the polysulphone polymer.

11. An electrochemical sensor for measuring pH in a fluid, comprising:
a working electrode, the working electrode comprising a conducting substrate, a first set of redox species, a second set of redox species and a polymer layer, wherein:
the first set of redox species comprises one or more non-polymeric redox species that are sensitive to pH;
the second set of redox species comprises one or more non-polymeric redox species that are insensitive to pH;
the first set of redox species is either chemically coupled with the conducting substrate, coated on the conducting substrate, directly immobilized on the conducting substrate or deposited on the conducting substrate and
the polymer layer consists of polymer and is disposed on top of the conducting substrate and the first set of redox species thereon, and wherein the polymer layer is configured to prevent diffusion of at least the first set of non-polymeric redox species from the working electrode and to allow hydrogen ions to diffuse through the polymer layer to interact with at least the first set of redox species;
a counter electrode;
a reference electrode;
means to apply a varying potential to the working electrode;
means to measure a potential difference between the working electrode and the reference electrode;
means to measure a current flow between the working electrode and the counter electrode as the applied potential causes the first and the second set of redox species to undergo at least one of oxidation and reduction; and
a processor configured to process a measurement of pH from at least one of the measured potential difference and the measured current.

12. The electrochemical sensor of claim 11, wherein the working electrode comprises a first working electrode and a second working electrode and the first working electrode comprises the first set of redox species and the second working electrode comprises the second set of redox species.

13. The electrochemical sensor of claim 11, wherein the second set of redox species is chemically coupled with the working electrode.

14. The electrochemical sensor of claim 11, wherein the second set of redox species is coated or deposited onto the working electrode.

15. The electrochemical sensor of claim 11, wherein the working electrode has a diameter between 1 and 5 millimeters and the polymer layer consists of less than 1000 micrograms of polymer.

16. The electrochemical sensor of claim 11, wherein the polymer layer consists of a polystyrene polymer.

17. The electrochemical sensor of claim 16, wherein the working electrode has a diameter between 1 and 5 millimeters and the polymer layer consists of less than 600 micrograms of the polystyrene polymer.

18. The electrochemical sensor of claim 16, wherein the working electrode has a diameter between 1 and 5 millimeters and the polymer layer consists of between 100 and 500 micrograms of the polystyrene polymer.

19. The electrochemical sensor of claim 11, wherein the polymer layer consists of a polysulphone polymer.

20. The electrochemical sensor of claim 19, wherein the working electrode has a diameter between 1 and 5 millimeters and the polymer layer consists of less than 600 micrograms of the polysulphone polymer.

21. The electrochemical sensor of claim 19, wherein the working electrode has a diameter between 1 and 5 millimeters and the polymer layer consists of between 10 and 500 micrograms of the polysulphone polymer.

22. The electrochemical sensor of claim 11, wherein the means for measuring at least one of the potential difference and the current flow comprises at least one of a voltammetric device and a potentiostat.

23. The electrochemical sensor of claim 11, wherein the one or more redox species sensitive to pH contains a hydroquinone or quinone moiety.

24. The electrochemical sensor in accordance with claim 11, wherein the one or more species insensitive to pH contain one of a ferrocene moiety, a ruthenocene moiety and a hexacyanometallate moiety.

25. The electrochemical sensor of claim 11, wherein a first surface area of the counter electrode is of the order of one to ten times that of a second surface area of the working electrode.

26. The electrochemical sensor of claim 11, wherein a first surface area of the counter electrode is less than one hundred times that of a second surface area of the working electrode.

27. The electrochemical sensor of claim 11, further comprising a temperature probe for measuring a temperature of the fluid.

28. The electrochemical sensor of claim 27, wherein the processor uses the temperature to process the presence or the measurement of the analyte.

29. The electrochemical sensor of claim 11, wherein the reference electrode comprises one of silver and silver chloride.

30. The electrochemical sensor of claim 12, wherein the second working electrode comprises carbon particles solvent cast with a ferrocene.

31. The electrochemical sensor of claim 11, wherein the processor processes the presence or measurement of pH from peak current flows produced by the oxidation or reduction of the first and the second sets of the redox species.

32. A method for electrochemically measuring pH of a fluid comprising:
contacting a working electrode with the fluid, wherein the working electrode comprises a conducting substrate coupled with a first set of redox species which comprises one or more non-polymeric redox species that are sensitive to pH wherein the coupling of the first set of redox species with the conducting substrate comprises one of the first set of redox species being chemically coupled with the conducting substrate, the first set of redox species being coated on the conducting substrate and the first set of redox species being deposited on the conducting substrate, a second set of non-polymeric redox species that are insensitive to pH and a polymer layer which consists of polymer and which directly covers at least an area of the conducting substrate where the conducting substrate is coupled with the redox species so that the polymer layer directly covers the redox species;
using the polymer layer to prevent diffusion of at least one of the first set of redox species and the second set of redox species from the working electrode;
applying a varying potential between the working electrode and a reference electrode;
making voltammetric measurements of at least a current flow between the working electrode and a counter electrode as the varying potential causes the first and the second set of redox species to undergo at least one of oxidation and reduction and a potential difference between the working electrode and the reference electrode; and processing the measurement of pH from the voltammetric measurements.

33. The method of claim 32, further comprising:

measuring a temperature of the fluid; and using the measured temperature to calibrate the measurement of pH.

\* \* \* \* \*